(12) United States Patent
Njar et al.

(10) Patent No.: US 11,707,468 B2
(45) Date of Patent: *Jul. 25, 2023

(54) METHODS OF TREATING PANCREATIC CANCER

(71) Applicant: UNIVERSITY OF MARYLAND, BALTIMORE, Baltimore, MD (US)

(72) Inventors: Vincent C. O. Njar, Glen Burnie, MD (US); Purushottamachar Puranik, Gaithersburg, MD (US); Andrew K. Kwegyir-Afful, Severn, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/861,529

(22) Filed: Apr. 29, 2020

(65) Prior Publication Data

US 2020/0261475 A1 Aug. 20, 2020

Related U.S. Application Data

(63) Continuation of application No. 15/516,113, filed as application No. PCT/US2015/053653 on Oct. 2, 2015, now Pat. No. 10,675,289.

(60) Provisional application No. 62/058,856, filed on Oct. 2, 2014.

(51) Int. Cl.
*A61K 31/58* (2006.01)
*C07J 43/00* (2006.01)
*A61K 45/06* (2006.01)
*A61P 35/00* (2006.01)
*A61K 31/7068* (2006.01)

(52) U.S. Cl.
CPC .......... *A61K 31/58* (2013.01); *A61K 31/7068* (2013.01); *A61K 45/06* (2013.01); *A61P 35/00* (2018.01); *C07J 43/003* (2013.01)

(58) Field of Classification Search
CPC ......... A61K 31/58; C07J 43/003; A61P 35/00
See application file for complete search history.

(56) References Cited

U.S. PATENT DOCUMENTS

| | | | |
|---|---|---|---|
| 2011/0319369 A1* | 12/2011 | Casebier | A61K 45/06 514/170 |
| 2013/0252930 A1 | 9/2013 | Chu et al. | |
| 2014/0066423 A1 | 3/2014 | Becker et al. | |
| 2015/0165177 A1* | 6/2015 | Giesing | A61K 45/06 514/49 |

FOREIGN PATENT DOCUMENTS

| | | |
|---|---|---|
| WO | 2011/059969 A2 | 5/2011 |
| WO | 2013/096907 A1 | 6/2013 |
| WO | 2014/153215 A1 | 9/2014 |
| WO | 2014/165815 A2 | 10/2014 |

OTHER PUBLICATIONS

Purushottamachar et al. (Journal of Medicinal Chemistry (published May 28, 2013) 56:4880-4898). (Year: 2013).*
Office Action, dated Jul. 10, 2020, issued in counterpart European patent application No. 15845704.4 (in English; 6 pages).
Office Action, dated Feb. 21, 2022, issued in counterpart European patent application No. 15845704.4 (in English; 3 pages).
Extended European Search Report, dated Feb. 2, 2018, issued in counterpart European patent application No. 15845704.4 (in English; 6 pages).
Cheng, H. et al., "Novel Agents for the Treatment of Pancreatic Adenocarcinoma", J Pancreas (Online), 12(4), pp. 334-338, Jul. 8, 2011 (in English; cited in EESR and ISR; 5 pages).
Cannon, J. "Analog Design", Fifth Edition, vol. I: Principles and Practice, Chapter Nineteen in Burger's Medicinal Chemistry and Drug Discovery, pp. 783-802, 1995 (in English, in U.S. Appl. No. 15/516,113).

\* cited by examiner

*Primary Examiner* — Marcos L Sznaidman
(74) *Attorney, Agent, or Firm* — Wenderoth, Lind & Ponack, L.L.P.

(57) ABSTRACT

Described herein are methods and compositions for the treatment of pancreatic cancer in a subject in need thereof. The pancreatic cancer may be resistant to other therapeutic regimens. The methods may comprise administering ARDA compounds to the subject.

14 Claims, 18 Drawing Sheets

METHODS OF TREATING PANCREATIC CANCER

CROSS-REFERENCE TO RELATED APPLICATIONS

This application is a continuation of U.S. patent application Ser. No. 15/516,113 filed on Mar. 31, 2017, which is a U.S. National Stage entry of International Application No. PCT/US2015/53653 filed on Oct. 2, 2015, which claims priority from U.S. Provisional Application No. 62/058,856 filed on Oct. 2, 2014, the entire disclosure of each of the foregoing is herein incorporated by reference.

GOVERNMENT SUPPORT

This invention was made with government support under Grant Numbers CA129379 and CA195694 awarded by the National Institutes of Health. The government has certain rights in the invention.

BACKGROUND

Cancer represents a significant burden on human health, accounting for an estimated 13% of all deaths each year. Several common cancers and diseases are associated with androgen signaling, such as, for example pancreatic cancer.

Pancreatic cancer is particularly aggressive and has a 3-5% survival rate. Histologically, 90% of human pancreatic cancer is presented as pancreatic ductal adenocarcinoma (PDAC). The aggressive nature of the disease and its high metastatic potential makes the development of efficacious therapeutic strategies very significant. Pancreatic ductal adenocarcinoma (PDAC) is the fourth leading cause of cancer death in the United States. In spite of recent therapeutic advances, long term survival in PDAC is often limited to patients who have had surgery in early stage of the disease. The biological aggressiveness of PDAC is due, in part, to the tumor's resistance to chemotherapy and to its propensity to metastasize even when the primary tumor is small.

SUMMARY

The present invention provides compositions and/or methods relating to treatment of cancer, e.g., pancreatic cancer, and particularly provides therapeutic regimens and/or modalities that utilize an androgen receptor downregulating and/or degrading agent, e.g., an "ARDA" or "ARDA compound" as described herein. The present disclosure particularly provides compositions and/or methods relating to galeterone, a known ARDA compound. Galeterone disrupts androgen receptor (AR) via three distinct mechanisms of action. Recent studies show that the molecule has the ability to also effectively modulate oncogenic eukaryotic protein translation via modulation of the mitogen activating protein kinase interacting kinase (Mnk)/eIF4E pathway and also inhibition of NF-κB activation. Because AR, Mnk/eIF4E and NF-icB have been implicated as important oncogenic targets causing proliferation, metastasis and in acquired drug resistance of pancreatic cancer cells, these unique mechanisms of Galeterone and its improved analogs, and ARDA compounds in general, may offer a multi-mechanistic advantage over current drugs in treating pancreatic cancer. Among other things, the present disclosure describes particular galeterone therapy regimens.

In one aspect, provided is a method comprising administering to a patient with pancreatic cancer a therapeutically effective amount of an ARDA compound or a pharmaceutically acceptable salt thereof.

In some embodiments, the ARDA compound is of formula (I)

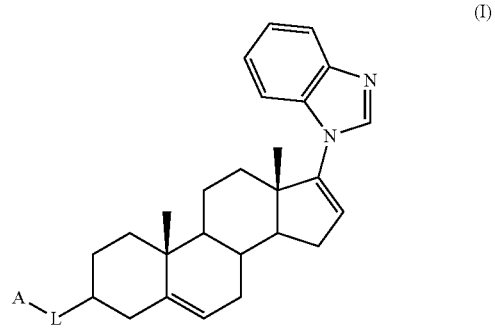

or a pharmaceutically acceptable salt thereof,
wherein
L is a covalent bond or a bivalent, straight or branched, optionally substituted $C_1$-$C_4$ alkylene; and
A is —OH, —OC(O)$CH_3$, imidazolyl or pyridyl, wherein the imidazolyl or pyridyl is optionally substituted with —$C_1$-$C_4$ alkyl, —O$C_1$-$C_4$ alkyl and/or -halogen.

In some embodiments, the ARDA compound is galeterone, i.e., the compound of formula:

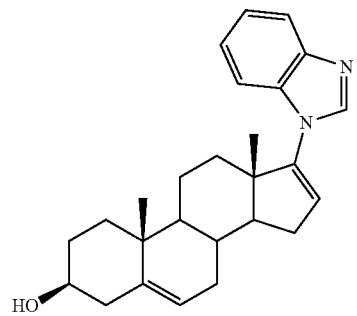 [SMILES: C[C@]12CC[C@H](O)CC1=CCC1C2CC[C@]2(C)C(n3cnc4ccccc43)=CCC12]

or a pharmaceutically acceptable salt thereof.

BRIEF DESCRIPTION OF THE DRAWING

(FIG. 4A) Clinical samples show poor survival for patients with an increased eIF4E phosphorylation. Survival Likelihood of PDA Patients: Group 0 comprise 8 patients with low p-eIF4E staining (score ≤2), group 1 comprise 24 patients with high p-eIF4E (score ≥3); P=0.02 at log-rank test. (FIG. 4B) Western blot data of MiaPaCa2 cells showing increased phosphorylation after gemcitabine treatment. (Adesso, L. et al. Oncogene 2013, 32, 2848-2857).

(FIG. 9A) Effect of Galeterone in combination with Gemcitabine on Gem-resistant PDAC cells. Galeterone combined with Gemcitabine at their respective $GI_{50}$ values and the CI values determined using calcusyn (CI<1-synergy, CI=1-additive and CI>1-antagonism. (FIG. 9B) Effect of VNPP433-313 in combination with Gemcitabine on Gem-resistant PDAC cells. VNPP433-313 combined with Gemcitabine at their respective $GI_{50}$ values and the CI values determined using calcusyn (CI<1-synergy, CI=1-additive and CI>1-antagonism.

(FIG. 16A) ASPC1 and gem-resistant cells were analyzed to investigate the effects on EZH2, Ras, p65 and nanog. (FIG. 16B) Knockdown of Mnk1 with siRNA shows downstream effects on MMP-2/9 and peIF4E.

(FIG. 17A) Western blot data in S2-013 cells. (FIG. 17B) Western blot data in S2VP10 cells. (FIG. 17C) Graphical representation of relative protein expression after treatment with control, Galeterone or VNPT55. (FIG. 17D) Graphical representation of cell cycle data (G2/M, S and G1) analyzed by flow cytometry in S2-013 cells.

(FIG. 18A) Galeterone and analogs induce apoptosis in S2-013 cells analyzed by acridine orange ethidium bromide staining. Cells were treated with 2.5 µM. (FIG. 18B) Galeterone and analogs were compared to gemcitabine in inducing apoptosis analyzed by flow cytometry in MiaPaCa-GR cells.

DEFINITIONS

Figure 1:
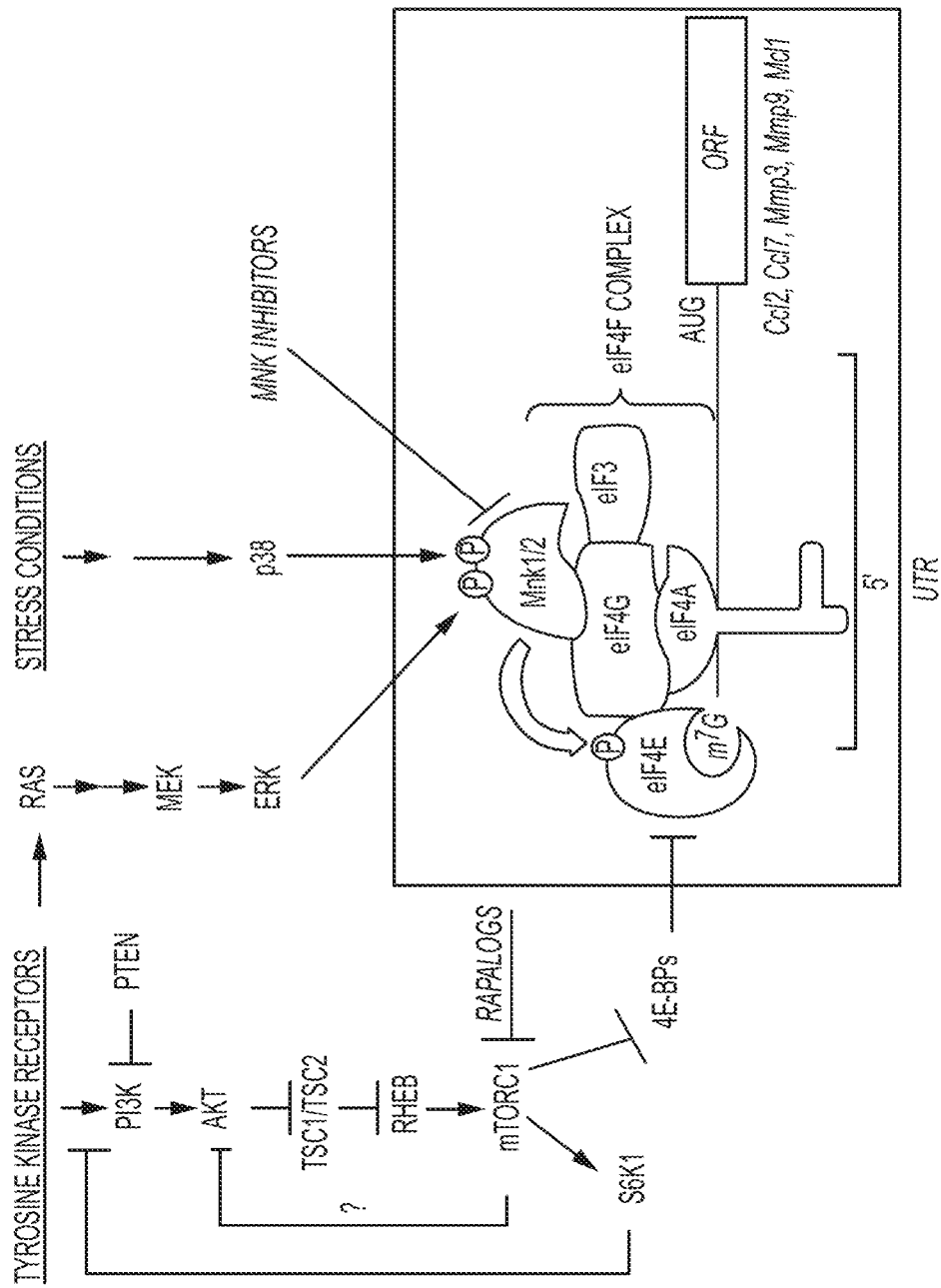
FIG. 1: Schematic illustration depicting the cellular pathways that lead to eIF4E activation and phosphorylation.

Administration: As used herein, the term "administration" refers to the administration of a composition to a subject or system (e.g., to a cell, organ, tissue, organism, or relevant component or set of components thereof). Those of ordinary skill will appreciate that, in some embodiments, route of administration may vary depending, for example, on the subject or system to which the composition is being administered, the nature of the composition, the purpose of the administration, etc. For example, in certain embodiments, administration to an animal subject (e.g., to a human) may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal and/or vitreal. In some embodiments, administration may involve intermittent dosing. In some embodiments, administration may involve continuous dosing (e.g., perfusion) for at least a selected period of time. In some embodiments, administration may be of a single dose. In some embodiments, administration may involve a plurality of doses (e.g., separated from one another in time).

Adult: As used herein, the term "adult" refers to a human eighteen years of age or older. In some embodiments, a human adult has a weight within the range of about 90 pounds to about 350 pounds.

Agent: The term "agent" as used herein may refer to a compound or entity of any chemical class including, for example, polypeptides, nucleic acids, saccharides, lipids, small molecules, metals, or combinations thereof. In some embodiments, an agent is or comprises a natural product in that it is found in and/or is obtained from nature. In some embodiments, an agent is or comprises one or more entities that is man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents are provided as collections or libraries, for example that may be screened to identify or characterize active agents within them. Some particular embodiments of agents that may be utilized in accordance with the present invention include small molecules, antibodies, antibody fragments, aptamers, nucleic acids (e.g., siRNAs, shRNAs, DNA/RNA hybrids, antisense oligonucleotides, ribozymes), peptides, peptide mimetics, etc. In some embodiments, an agent is or comprises a polymer. In some embodiments, an agent is not a polymer and/or is substantially free of any polymer. In some embodiments, an agent contains at least one polymeric moiety. In some embodiments, an agent lacks or is substantially free of any polymeric moiety.

Allele: As used herein, the term "allele" refers to one of two or more existing genetic variants of a specific polymorphic genomic locus.

Analog: As used herein, the term "analog" refers to a substance that shares one or more particular structural features, elements, components, or moieties with a reference substance. Typically, an "analog" shows significant structural similarity with the reference substance, for example sharing a core or consensus structure, but also differs in certain discrete ways. In some embodiments, an analog is a substance that can be generated from the reference substance, e.g., by chemical manipulation of the reference substance. In some embodiments, an analog is a substance that can be generated through performance of a synthetic process substantially similar to (e.g., sharing a plurality of steps with) one that generates the reference substance. In some embodiments, an analog is or can be generated through performance of a synthetic process different from that used to generate the reference substance.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: Two events or entities are "associated" with one another, as that term is used herein, if the presence, level and/or form of one is correlated with that of the other. For example, a particular entity (e.g., polypeptide, genetic signature, metabolite, etc.) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Binding: It will be understood that the term "binding", as used herein, typically refers to a non-covalent association between or among two or more entities. "Direct" binding involves physical contact between entities or moieties; indirect binding involves physical interaction by way of physical contact with one or more intermediate entities. Binding between two or more entities can typically be assessed in any of a variety of contexts—including where interacting entities or moieties are studied in isolation or in the context of more complex systems (e.g., while covalently or otherwise associated with a carrier entity and/or in a biological system or cell).

Biological Sample: As used herein, the term "biological sample" typically refers to a sample obtained or derived from a biological source (e.g., a tissue or organism or cell culture) of interest, as described herein. In some embodiments, a source of interest comprises an organism, such as an animal or human. In some embodiments, a biological sample is or comprises biological tissue or fluid. In some embodiments, a biological sample may be or comprise bone marrow; bone, teeth, blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, obtained cells are or include cells from an individual from whom the sample is obtained. In some embodiments, a sample includes circulating tumor cells ("CTC"). In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, post Whipple procedure, collection of body fluid (e.g., blood, lymph, CSF, feces etc.), etc. In some embodiments, as will be clear from context, the term "sample" refers to a preparation that is obtained by processing (e.g., by removing one or more components of and/or by adding one or more agents to) a primary sample. For example, filtering using a semipermeable membrane, antibody capture, cell sorting. Such a "processed sample" may comprise, for example nucleic acids or proteins extracted from a sample or obtained by subjecting a primary sample to techniques such as amplification or reverse transcription of mRNA, isolation and/or purification of certain components, etc.

Biomarker: The term "biomarker" is used herein, consistent with its use in the art, to refer to a to an entity whose presence, level, or form, correlates with a particular biological event or state of interest, so that it is considered to be a "marker" of that event or state. To give but a few examples, in some embodiments, a biomarker may be or comprises a marker for a particular disease state, or for likelihood that a particular disease, disorder or condition may develop. In some embodiments, a biomarker may be or comprise a marker for a particular disease or therapeutic outcome, or likelihood thereof. Thus, in some embodiments, a biomarker is predictive, in some embodiments, a biomarker is prognostic, in some embodiments, a biomarker is diagnostic, of the relevant biological event or state of interest. A biomarker may be an entity of any chemical class. For example, in some embodiments, a biomarker may be or comprise a nucleic acid, DNA, RNA, microRNA, mRNA, an amino acid, a polypeptide, a protein, a lipid, phospholipid, a carbohydrate, polysaccharide, a small molecule, an inorganic agent (e.g., a metal or ion), or a combination thereof. In some embodiments, a biomarker is a cell surface marker. In some embodiments, a biomarker is intracellular. In some embodiments, a biomarker is found outside of cells (e.g., is secreted or is otherwise generated or present outside of cells, e.g., in a body fluid such as blood, urine, tears, saliva, feces, lymph, nasal mucosa, cerebrospinal fluid, etc.

Cancer: The terms "cancer", "malignancy", "neoplasm", "tumor", and "carcinoma", are used interchangeably herein to refer to cells that exhibit relatively abnormal, uncontrolled, and/or autonomous growth, so that they exhibit an aberrant growth phenotype characterized by a significant loss of control of cell proliferation. In general, cells of interest for detection or treatment in the present application include precancerous (e.g., benign), malignant, pre-metastatic, metastatic, and non-metastatic cells. The teachings of the present disclosure may be relevant to any and all cancers. To give but a few, non-limiting examples, in some embodiments, teachings of the present disclosure are applied to one or more cancers such as, for example, hematopoietic cancers including leukemias, lymphomas (Hodgkins and non-Hodgkins), myelomas and myeloproliferative disorders; sarcomas, melanomas, adenomas, carcinomas of solid tissue, squamous cell carcinomas of the mouth, throat, larynx, and lung, liver cancer, genitourinary cancers such as prostate, cervical, bladder, uterine, and endometrial cancer and renal cell carcinomas, bone cancer, pancreatic cancer, skin cancer, cutaneous or intraocular melanoma, cancer of the endocrine system, cancer of the thyroid gland, cancer of the parathyroid gland, head and neck cancers, breast cancer, gastrointestinal cancers, brain cancer, nervous system cancers, and benign lesions such as papillomas, and the like.

Chemotherapeutic Agent: The term "chemotherapeutic agent", has used herein has its art-understood meaning referring to one or more pro-apoptotic, cytostatic and/or cytotoxic agents, for example specifically including agents utilized and/or recommended for use in treating one or more diseases, disorders or conditions associated with undesirable cell proliferation. In many embodiments, chemotherapeutic agents are useful in the treatment of cancer. In some embodiments, a chemotherapeutic agent may be or comprise one or more agents selected from the group consisting of alkylating agents (and/or other DNA modifying agents), anthracyclines, cytoskeletal disruptors (e.g. microtubule targeting agents and/or disrupting agents such as, for example, taxanes, maytansine and analogs thereof, of), epothilones, histone deacetylase inhibitors ("HDACs"), topoisomerase inhibitors (e.g., inhibitors of topoisomerase I and/or topoisomerase II), kinase inhibitors, nucleotide analogs, nucleotide precursor analogs, peptide antibiotics, platinum-based agents, retinoids, *vinca* alkaloids, analogs of the foregoing (i.e., that share a relevant anti-proliferative activity), and combinations thereof. In some particular embodiments, a chemotherapeutic agent may be or comprise one or more of Actinomycin, All-trans retinoic acid, Auiristatin, Azacitidine, Azathioprine, Bleomycin, Bortezomib, Calicheamicin, Carboplatin, Capecitabine, Centanamycin, Cisplatin, Chlorambucil, Cyclophosphamide, Curcumin, Cytarabine, Daunorubicin, Docetaxel, Dolastatin, Doucarmycin, Doxifluridine, Doxorubicin, Epirubicin, Epothilone, Etoposide, Fluorouracil, Gemcitabine, Hydroxyurea, Idarubicin, Imatinib, Irinotecan, Maytansine, Mechlorethamine, Mercaptopurine, Methotrexate, Mitoxantrone, a Maytansinoid, Oxaliplatin, Paclitaxel, Pemetrexed, Pyrrolobenzydiazepines, Teniposide, Tioguanine, Topotecan, Valrubicin, Vinblastine, Vincristine, Vindesine, Vinorelbine, analogs of any of the foregoing (e.g., Monomethyl Auristatin E and/or Monomethyl Auristatin F, which are analogs of Auristatin, DM1 and/or DM4, which are analogs of Maytansinoid, etc), and combinations thereof. In some embodiments, a chemotherapeutic agent may be utilized in the context of an antibody-drug conjugate. In some embodiments, a chemotherapeutic agent is one found in an antibody-drug conjugate selected from the group consisting of ABT-414, AGS-15E, AGS-16C3F (AGS 16C3F/AGS-16M8F), AGS-16M8F (AGS 16C3F/AGS-16C3F), AGS-22M6E, AMG172, AMG-595, Anti-ETBR (RG-7636), Anti-PSMA ADC, ARX788 HER2 ADC, ASG-15ME, ASG-16M8F, ASG-22CE, ASG-22ME, ASG-5ME, BAY79-4620 (3ee9/BAY 794620/BAY 79-4620), BAY-94-9343, BIIB-015, Brentuximab vedotin (SGN35/Adcetris®), BT062, Coltuximab Ravtansine (SAR 3419), DEDN6526A (RG-7636/RG7636), Denintuzumab mafodotin (SGN-CD19A/SGN-19A), DMOT4039A (DMOT-4039A/RG7600/RG 7600), Enfortumab Vedotin (ASG-22ME/ASG-22MSE), Epratuzumab-SN-38, Gemtuzumab ozogamicin, Glembatumomab vedotin (CDX-011), GSK2857916 (J6MO-mcMMAF), hA20-Pro-2-P-Dox, hA20-SN-38, hLL1-doxorubicin, hLL1-Pro-2-P-Dox, hLL1-SN-38, hLL2-Pro-2-P-Dox, hLL2-SN-38, hMN-14-Pro-2-P-Dox, hMN-14-SN-38, hPAM4-Pro-2-P-Dox, hPAM4-SN-38, hRS7-Pro-2-P-Dox, hRS7-SN-38, HuMax-TF-ADC (TF-011-MMAE), IGN523, IMGN 289, IMGN 779, IMGN-242, IMGN-388, IMGN-529 (K7153A), IMGN-633 (AVE9633), IMGN-853, Indatuximab Ravtansine (BT-062), Indusatumab vedotin (MLN-0264), Inotuzumab ozogamicin (CMC-544), Labetuzumab-SN-38 (IMMU-130)(hMN-14-SN38), Lifastuzumab Vedotin (Anti-NaPi2b ADC/RG-7599/DNIB0600A), LOP628 (LOP-628), Lorvotuzumab mertansine (IMGN-901), MDX-1203, MEDI-547, MI130004, Milatuzumab-doxorubic in (hLL1-DOX), MLN-0264, MLN-2704, P4/D10-doxorubicin, PF 06263507 (A1-mcMMAF/Anti-5T4 monoclon antibody-Pfizer/PF-06263507, Pinatuzumab vedotin (RG-7593/DCDT2980S/DCDT-2989S), Polatuzumab vodotin (RG-7596/DCDS4501A/DCDS-4501A), PSMA-ADC, RG-7450, RG-7458, RG-7593, RG-7596, RG-7598 (DFRF 4539A/RG7598/RG 7598), RG-7599, RG-7600, RG-7636, RG-7841, Sacituzumab govitecan (IMMU-132/hRS7-SN38), SAR3419, SAR566658, SC16LD6.5, SGN CD70 A (superseding SGN-75), SGN-15 (BMS-182248, BR96-DOX), SGN-75, SGN-CD19A, SGN-CD33A (EC-mAb), SGN-LIV1A (Anti-LIV-1 ADC), Sofituzumab vedotin (Anti-MUC16 ADC/RG7458 DMUC5754A), SYD985, Trastuzumab emtansine (T-DM1), trastuzumab maytansinoid, Vandortuzumab vedotin (Anti-STEAP1 DC/RG7450/DSTP3086S/MSTP2109A), Vintafolide (EC145/MK 8109, Vorsetuzumab mafodotin (SGN-75). In some embodiments, a chemotherapeutic agent may be one described as utilized in an antibody-drug conjugate as described or discussed in one or more of Govindan et al, The Scientific World JOURNAL 10:2070, 2010 and/or at www://http://adcreview.com/knowledge-center/adc-drugmap/).

Circulating Tumor Cell: As used herein a circulating tumor cell is a tumor cell that is found the blood stream, for example having been shed into the vasculature.

Combination therapy: As used herein, the term "combination therapy" refers to those situations in which a subject is simultaneously exposed to two or more therapeutic regimens (e.g., two or more therapeutic agents). In some embodiments, two or more agents or may be administered simultaneously; in some embodiments, such agents may be administered sequentially; in some embodiments, such agents are administered in overlapping dosing regimens.

Comparable: The term "comparable" is used herein to describe two (or more) sets of conditions, circumstances, individuals, or populations that are sufficiently similar to one another to permit comparison of results obtained or phenomena observed. In some embodiments, comparable sets of conditions, circumstances, individuals, or populations are characterized by a plurality of substantially identical features and one or a small number of varied features. Those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied. Those skilled in the art will appreciate that relative language used herein (e.g., enhanced, activated, reduced, inhibited, etc.) will typically refer to comparisons made under comparable conditions.)

Composition: A "composition" or a "pharmaceutical composition" according to this invention refers to the combination of two or more agents as described herein for co-administration or administration as part of the same regimen. It is not required in all embodiments that the combination of agents result in physical admixture, that is, administration as separate co-agents each of the components of the composition is possible; however many patients or practitioners in the field may find it advantageous to prepare a composition that is an admixture of two or more of the ingredients in a pharmaceutically acceptable carrier, diluent, or excipient, making it possible to administer the component ingredients of the combination at the same time.

Comprising: A composition or method described herein as "comprising" one or more named elements or steps is open-ended, meaning that the named elements or steps are essential, but other elements or steps may be added within the scope of the composition or method. To avoid prolixity, it is also understood that any composition or method described as "comprising" (or which "comprises") one or more named elements or steps also describes the corresponding, more limited composition or method "consisting essentially of" (or which "consists essentially of") the same named elements or steps, meaning that the composition or method includes the named essential elements or steps and may also include additional elements or steps that do not materially affect the basic and novel characteristic(s) of the composition or method. It is also understood that any composition or method described herein as "comprising" or "consisting essentially of" one or more named elements or steps also describes the corresponding, more limited, and closed-ended composition or method "consisting of" (or "consists of") the named elements or steps to the exclusion of any other unnamed element or step. In any composition or method disclosed herein, known or disclosed equivalents of any named essential element or step may be substituted for that element or step.

Determine: Certain methodologies described herein include a step of "determining". Those of ordinary skill in the art, reading the present specification, will appreciate that such "determining" can utilize or be accomplished through use of any of a variety of techniques available to those skilled in the art, including for example specific techniques explicitly referred to herein. In some embodiments, determining involves manipulation of a physical sample. In some embodiments, determining involves consideration and/or manipulation of data or information, for example utilizing a computer or other processing unit adapted to perform a relevant analysis. In some embodiments, determining involves receiving relevant information and/or materials from a source. In some embodiments, determining involves comparing one or more features of a sample or entity to a comparable reference.

Dosage Form: As used herein, the term "dosage form" refers to a physically discrete unit of an active agent (e.g., a therapeutic or diagnostic agent) for administration to a subject. Each unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or agent administered to a particular subject is determined by one or more attending physicians and may involve administration of multiple dosage forms.

Diagnostic information: As used herein, "diagnostic information" or "information for use in diagnosis" is information that is useful in determining whether a patient has a disease, disorder or condition and/or in classifying a disease, disorder or condition into a phenotypic category or any category having significance with regard to prognosis of a disease, disorder or condition, or likely response to treatment (either treatment in general or any particular treatment) of a disease, disorder or condition. Similarly, "diagnosis" refers to providing any type of diagnostic information, including, but not limited to, whether a subject is likely to have or develop a disease, disorder or condition, state, staging or characteristic of a disease, disorder or condition as manifested in the subject, information related to the nature or classification of a tumor, information related to prognosis and/or information useful in selecting an appropriate treatment (safety, efficacy, toxicity, pharmacokinetic, drug-drug interactions). Selection of treatment may include the choice of a particular therapeutic agent or other treatment modality such as surgery, post Whipple procedure, radiation, etc., a choice about whether to withhold or deliver therapy, a choice relating to dosing regimen (e.g., frequency or level of one or more doses of a particular therapeutic agent or combination of therapeutic agents), etc.

Dosage form: and "unit dosage form", as used herein, the term "dosage form" refers to physically discrete unit of a therapeutic agent for a subject (e.g., a human patient) to be treated. Each unit contains a predetermined quantity of active material calculated or demonstrated to produce a desired therapeutic effect when administered to a relevant population according to an appropriate dosing regimen. For example, in some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). It will be understood, however, that the total dosage administered to any particular patient will be selected by a medical professional (e.g., a medical doctor) within the scope of sound medical judgment.

Dosing regimen: (or "therapeutic regimen"), as used herein is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, the therapeutic agent is administered continuously (e.g., by infusion) over a predetermined period. In some embodiments, a therapeutic agent is administered once a day (QD) or twice a day (BID). In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount In some embodiments, a dosing regimen is correlated with a desired or beneficial outcome when administered across a relevant population (i.e., is a therapeutic dosing regimen).

Excipient: as used herein, refers to a non-therapeutic agent that may be included in a pharmaceutical composition, for example to provide or contribute to a desired consistency or stabilizing effect. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein.

Improve," "increase" or "reduce": As used herein or grammatical equivalents thereof, indicate values that are relative to a baseline measurement, such as a measurement in the same individual prior to initiation of a treatment described herein, or a measurement in a control individual (or multiple control individuals) in the absence of the treatment described herein. A "control individual" is an individual afflicted with the same form of disease or injury as the individual being treated.

Marker: A marker, as used herein, refers to an entity or moiety whose presence or level is a characteristic of a particular state or event. In some embodiments, presence or level of a particular marker may be characteristic of presence or stage of a disease, disorder, or condition. To give but one example, in some embodiments, the term refers to a gene expression product that is characteristic of a particular tumor, tumor subclass, stage of tumor, etc. Alternatively or additionally, in some embodiments, a presence or level of a particular marker correlates with activity (or activity level) of a particular signaling pathway, for example that may be characteristic of a particular class of tumors. The statistical significance of the presence or absence of a marker may vary depending upon the particular marker. In some embodiments, detection of a marker is highly specific in that it reflects a high probability that the tumor is of a particular subclass. Such specificity may come at the cost of sensitivity (i.e., a negative result may occur even if the tumor is a tumor that would be expected to express the marker). Conversely, markers with a high degree of sensitivity may be less specific that those with lower sensitivity. According to the present invention a useful marker need not distinguish tumors of a particular subclass with 100% accuracy.

Patient: As used herein, the term "patient" or "subject" refers to any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre- and post-natal forms. In some embodiments, a patient is suffering from or susceptible to one or more disorders or conditions. In some embodiments, a patient displays one or more symptoms of a disorder or condition. In some embodiments, a patient has been diagnosed with one or more disorders or conditions.

Pharmaceutically Acceptable: As used herein, the term "pharmaceutically acceptable" applied to the carrier, diluent, or excipient used to formulate a composition as disclosed herein means that the carrier, diluent, or excipient must be compatible with the other ingredients of the composition and not deleterious to the recipient thereof.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. In some embodiments, a pharmaceutically acceptable carrier may be or comprise polyvinylpyrrolidone (copovidone).

Pharmaceutically acceptable salt: As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations formed using counterions such as halide, hydroxide, carboxylate, sulfate, phosphate, nitrate, lower alkyl sulfonate and aryl sulfonate.

Pharmaceutical composition: As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and/or to other mucosal surfaces.

Prevention: The term "prevention", as used herein, refers to a delay of onset, and/or reduction in frequency and/or severity of one or more symptoms of a particular disease, disorder or condition. In some embodiments, prevention is assessed on a population basis such that an agent is considered to "prevent" a particular disease, disorder or condition if a statistically significant decrease in the development, frequency, and/or intensity of one or more symptoms of the disease, disorder or condition is observed in a population susceptible to the disease, disorder, or condition. Prevention may be considered complete when onset of a disease, disorder or condition has been delayed for a predefined period of time.

Prognostic and predictive information: As used herein, the terms "prognostic information" and "predictive information" are used to refer to any information that may be used to indicate any aspect of the course of a disease or condition either in the absence or presence of treatment. Such information may include, but is not limited to, the average life expectancy of a patient, the likelihood that a patient will survive for a given amount of time (e.g., 6 months, 1 year, 5 years, etc.), the likelihood that a patient will be cured of a disease, the likelihood that a patient's disease will respond to a particular therapy (wherein response may be defined in any of a variety of ways). Prognostic and predictive information are included within the broad category of diagnostic information.

Reference: as used herein describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Refractory: The term "refractory" as used herein, refers to any patient or subject or condition that does not respond with an expected clinical efficacy following the administration of provided compositions as normally observed by practicing medical personnel.

Response: As used herein, a response to treatment may refer to any beneficial alteration in a subject's condition that occurs as a result of or correlates with treatment. Such alteration may include stabilization of the condition (e.g., prevention of deterioration that would have taken place in the absence of the treatment), amelioration of symptoms of the condition, and/or improvement in the prospects for cure of the condition, etc. It may refer to a subject's response or to a tumor's response. Tumor or subject response may be measured according to a wide variety of criteria, including clinical criteria and objective criteria. Techniques for assessing response include, but are not limited to, clinical examination, positron emission tomatography (PET), positron emission tomatography-computed tomography (PET-CT); chest X-ray CT scan, MRI, ultrasound, endoscopy, laparoscopy, presence or level of tumor markers in a sample obtained from a subject, cytology, and/or histology. Many of these techniques attempt to determine the size of a tumor or otherwise determine the total tumor burden. Methods and guidelines for assessing response to treatment are discussed in Therasse et. al., "New guidelines to evaluate the response to treatment in solid tumors", European Organization for Research and Treatment of Cancer, National Cancer Institute of the United States, National Cancer Institute of Canada, J. Natl. Cancer Inst., 2000, 92(3):205-216. The exact response criteria can be selected in any appropriate manner, provided that when comparing groups of tumors and/or patients, the groups to be compared are assessed based on the same or comparable criteria for determining response rate. One of ordinary skill in the art will be able to select appropriate criteria.

Sample: As used herein, the term "sample" typically refers to a biological sample obtained or derived from a source of interest, as described herein. In some embodiments, a source of interest comprises an organism, such as an animal or human. In some embodiments, a biological sample is or comprises biological tissue or fluid. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid; peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, obtained cells are or include cells from an individual from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc.

Solid Tumor: As used herein, the term "solid tumor" refers to an abnormal mass of tissue that usually does not contain cysts or liquid areas. Solid tumors may be benign or malignant. Different types of solid tumors are named for the type of cells that form them. Examples of solid tumors are sarcomas, carcinomas, lymphomas, mesothelioma, neuroblastoma, retinoblastoma, etc.

Stage of cancer: As used herein, the term "stage of cancer" refers to a qualitative or quantitative assessment of the level of advancement of a cancer. Criteria used to determine the stage of a cancer include, but are not limited to, the size of the tumor and the extent of metastases (e.g., localized or distant).

Subject: As used herein, means any mammal, including humans. In certain embodiments of the present invention the subject is an adult, an adolescent or an infant. In some embodiments, terms "individual" or "patient" are used and are intended to be interchangeable with "subject". Also contemplated by the present invention are the administration of the pharmaceutical compositions and/or performance of the methods of treatment in-utero.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Surrogate Marker: The term "surrogate marker", as used herein, refers to an entity whose presence, level, or form, may act as a proxy for presence, level, or form of another entity (e.g., a biomarker) of interest. Typically, a surrogate marker may be easier to detect or analyze (e.g., quantify) than is the entity of interest. To give but one example, in some embodiments, where the entity of interest is a protein, an expressed nucleic acid (e.g., mRNA) encoding the protein may sometimes be utilized as a surrogate marker for the protein (or its level). To give another example, in some embodiments, where the entity of interest is an enzyme, a product of the enzyme's activity may sometimes be utilized as a surrogate marker for the enzyme (or its activity level). To give one more example, in some embodiments, where the entity of interest is a small molecule, a metabolite of the small molecule may sometimes be used as a surrogate marker for the small molecule. To give one more example, a surrogate marker may be a clinically observed feature or stemming from a patient observation, e.g. changes in fatigue, stamina, memory, daily routine, etc.

Therapeutic Agent: As used herein, the phrase "therapeutic agent" in general refers to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc. In some embodiments, a therapeutic agent is a substance that can be used to alleviate, ameliorate, relieve, inhibit, prevent, delay onset of, reduce severity of, and/or reduce incidence of one or more symptoms or features of a disease, disorder, and/or condition. In some embodiments, a "therapeutic agent" is an agent that has been or is required to be approved by a government agency before it can be marketed for administration to humans. In some embodiments, a "therapeutic agent" is an agent for which a medical prescription is required for administration to humans.

Therapeutic regimen: A "therapeutic regimen", as that term is used herein, refers to a dosing regimen whose administration across a relevant population may be correlated with a desired or beneficial therapeutic outcome.

Therapeutically effective amount: As used herein, is meant an amount that produces the desired effect for which it is administered. In some embodiments, the term refers to an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in some embodiments, a therapeutically effective amount of a particular agent or therapy may be formulated and/or administered in a single dose. In some embodiments, a therapeutically effective agent may be formulated and/or administered in a plurality of doses, for example, as part of a dosing regimen.

Treatment: As used herein, the term "treatment" (also "treat" or "treating"), in its broadest sense, refers to any administration of a substance (e.g., provided compositions) that partially or completely alleviates, ameliorates, relives, inhibits, delays onset of, reduces severity of, and/or reduces incidence of one or more symptoms, features, and/or causes of a particular disease, disorder, and/or condition. In some embodiments, such treatment may be administered to a subject who does not exhibit signs of the relevant disease, disorder and/or condition and/or of a subject who exhibits only early signs of the disease, disorder, and/or condition. Alternatively or additionally, in some embodiments, treatment may be administered to a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

Unit dose: The expression "unit dose" as used herein refers to an amount administered as a single dose and/or in a physically discrete unit of a pharmaceutical composition. In many embodiments, a unit dose contains a predetermined quantity of an active agent. In some embodiments, a unit dose contains an entire single dose of the agent. In some embodiments, more than one unit dose is administered to achieve a total single dose. In some embodiments, administration of multiple unit doses is required, or expected to be required, in order to achieve an intended effect. A unit dose may be, for example, a volume of liquid (e.g., an acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be appreciated that a unit dose may be present in a formulation that includes any of a variety of components in addition to the therapeutic agent(s). For example, acceptable carriers (e.g., pharmaceutically acceptable carriers), diluents, stabilizers, buffers, preservatives, etc., may be included as described infra. It will be appreciated by those skilled in the art, in many embodiments, a total appropriate daily dosage of a particular therapeutic agent may comprise a portion, or a plurality, of unit doses, and may be decided, for example, by the attending physician within the scope of sound medical judgment. In some embodiments, the specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts.

Administering . . . with regard to food intake: As used herein, the term "administering . . . with regard to food intake" refers to an administration, e.g., of a therapy regimen to a subject or population of patients, where the subject or population of patients is known to have consumed, or not consumed, some amount of food before, during or after the administration. The terms "before administration" and "after administration" with respect to food intake may refer to a period of time of about 1, 2, 3, 4, 5, 6, 7, 8, 9, 10, 11, 12, 14, 16, 18, 20, 22, 24, 30, 42, or 72 hours, or longer, before or after the administration. In some embodiments, food intake includes high fat foods or a high fat diet.

In some embodiments, the term "administering . . . with regard to food intake" implies that the subject or population of patients consumes food before the administration. In some embodiments, the term "administering . . . with regard to food intake" implies that the subject or population of patients consumes food after the administration. In some embodiments, the term "administering . . . with regard to food intake" implies that the subject or population of patients consumes food during the administration. Alternatively, in some embodiments, the term "administering . . . with regard to food intake" means the subject or population of patients is in a fasted state during administration.

Administering . . . without regard to food intake: As used herein, the term "administering . . . without regard to food intake" refers to an administration, e.g., of a therapy regimen to a subject or population of patients, regardless of whether the subject or population of patients has consumed, or not consumed, some amount of food before, during or after the administration.

DETAILED DESCRIPTION OF CERTAIN EMBODIMENTS

Pancreatic Cancer

Pancreatic cancer (pancreatic ductal adenocarcinoma, PDAC) is one of the most lethal malignant diseases with poor prognosis. PDAC is the $4^{th}$ most common cause of cancer-related deaths in both men and women in the United States. PDAC is a highly aggressive epithelial cancer with a reported 5-year survival rate of ~5% (7). Only 20% of pancreatic cancer patients are eligible for surgical resection, and metastatic disease frequently develops even after surgery, while current chemo- and radio-therapies are largely ineffective (8). Therefore, understanding the molecular events underlying the development, progression of PDAC and resistance to current therapy is needed.

Testosterone may have a positive effect on the growth of pancreatic carcinoma. This would be supported if specific androgen receptor blockade improved survival. The concept is supported by the presence of androgen receptors within human pancreatic cancer tissue, together with the enzymes, aromatase and 5α-reductase, which converts testosterone into either oestradiol or a more active androgen, 5α-dihydrotestosterone, respectively. Furthermore, all patients with pancreatic cancer have low serum testosterone concentrations. Confirmatory evidence for the role of testosterone came with the demonstration of its growth potentiating action on human pancreatic adencocarcinoma xenografts grown in nude mice, together with the inhibiting action of an antiandrogen (23).

Because pancreatic cancer is a major public health concern, the development of new therapeutic strategies for the treatment of this devastating disease is challenging and significant. Current therapeutic strategies are ineffective as the deregulated RAS/MAPK and PI3K-AKT-mTOR pathways enhance drug resistance. Gemcitabine alone or in combination with erlotinib, currently used drugs for PDAC, elicit only marginal survival benefits. The modest efficacy of gemcitabine therapy has been attributed to activation of the NFκB pathway which activates genes involved in gemcitabine resistance.

The PI3K-AKT-mTOR and MAPK pathways are deregulated in pancreatic cancer. Recent studies have also implicated the downstream signaling component of these pathways, eIF4F (specifically, eIF4E-Mnk1/2 axis) which controls gene expression at the translational level towards PDAC development and to de novo and acquired drug resistant. The significance of this finding is underscored by the tremendous therapeutic potential for targeting this downstream oncogenic nexus in human PDAC and indeed other cancers impacted by these dysfunctions.

A potentially curative treatment of pancreatic ductal adenocarcinoma is surgery, but only 15%-20% of patients are eligible. Major limiting factors are the patients' general condition and an already locally advanced or metastatic disease. Five-year overall survival rates vary between 1% and 4%. Even after surgical resection plus adjuvant chemotherapy, overall survival rates do not exceed 25%-30%. (Jemal A, et al. C A *Cancer J Clin* 2010; 60:277-300).

Various treatment regimens failed to improve survival of patients. Gemcitabine (GEMZAR®) is anti-cancer chemotherapy drug used for the treatment of pancreatic cancer. Weekly intravenous administration of gemcitabine has been shown to be effective and was approved in 1998 by the US FDA for pancreatic cancer. The US FDA has also approved the kinase inhibitor erlotinib for use in combination with gemcitabine for patients with advanced-stage pancreatic cancer who have not received previous chemotherapy. However, the median overall survival benefit derived from erlotinib is only less than four weeks. (Moore et al., *J. Clin. Oncol.*, 2007; 25(15):1960-6). Many efforts aimed at improving single-agent Gemcitabine efficacy by either combining it with a second cytotoxic/molecularly targeted agent or pharmacokinetic modulation provided disappointing results.

Multi-targeted single-agents and drug combinations are an emerging class of pancreatic (pancreatic ductal adenocarcinoma, PDAC) therapeutics. By inhibiting multiple oncogenic targets simultaneously, they offer a major advantage over single-target drugs. Because PDAC is highly aggressive with a characteristically increased metastatic potential, the development of new and efficacious therapeutic strategies against the disease is significant and desirable. Gemcitabine (Gem) and Folfirinox are the respective elective single-agent and drug combinations in PDAC chemotherapy. These drugs exert only marginal survival benefits, urging the identification of new drugs and/or therapeutic targets. The modest efficacy of gemcitabine therapy has been attributed to activation of the NF-κB pathway which activates genes involved in gemcitabine resistance. Recent studies have implicated the eIF4E-Mnk1/2 axis in gemcitabine resistance. Several preclinical and clinical studies have implicated the involvement of the androgen receptor in PDAC progression and a few clinical trials with anti-androgens have shown promising results.

Figure 2:
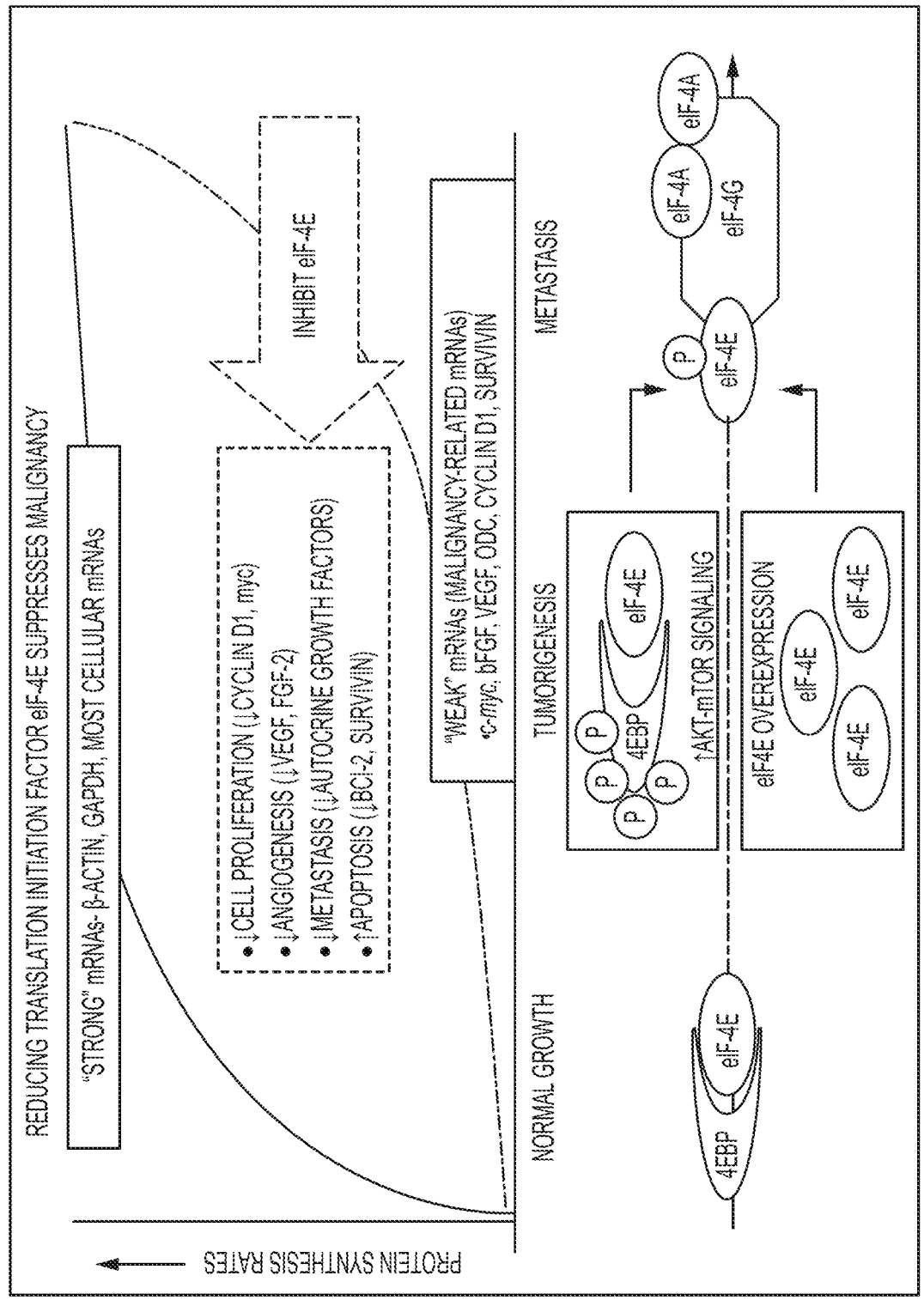
FIG. 2: Schematic illustration depicting how reducing translation initiation factor eIF4E suppresses malignancy.
Figure 3:
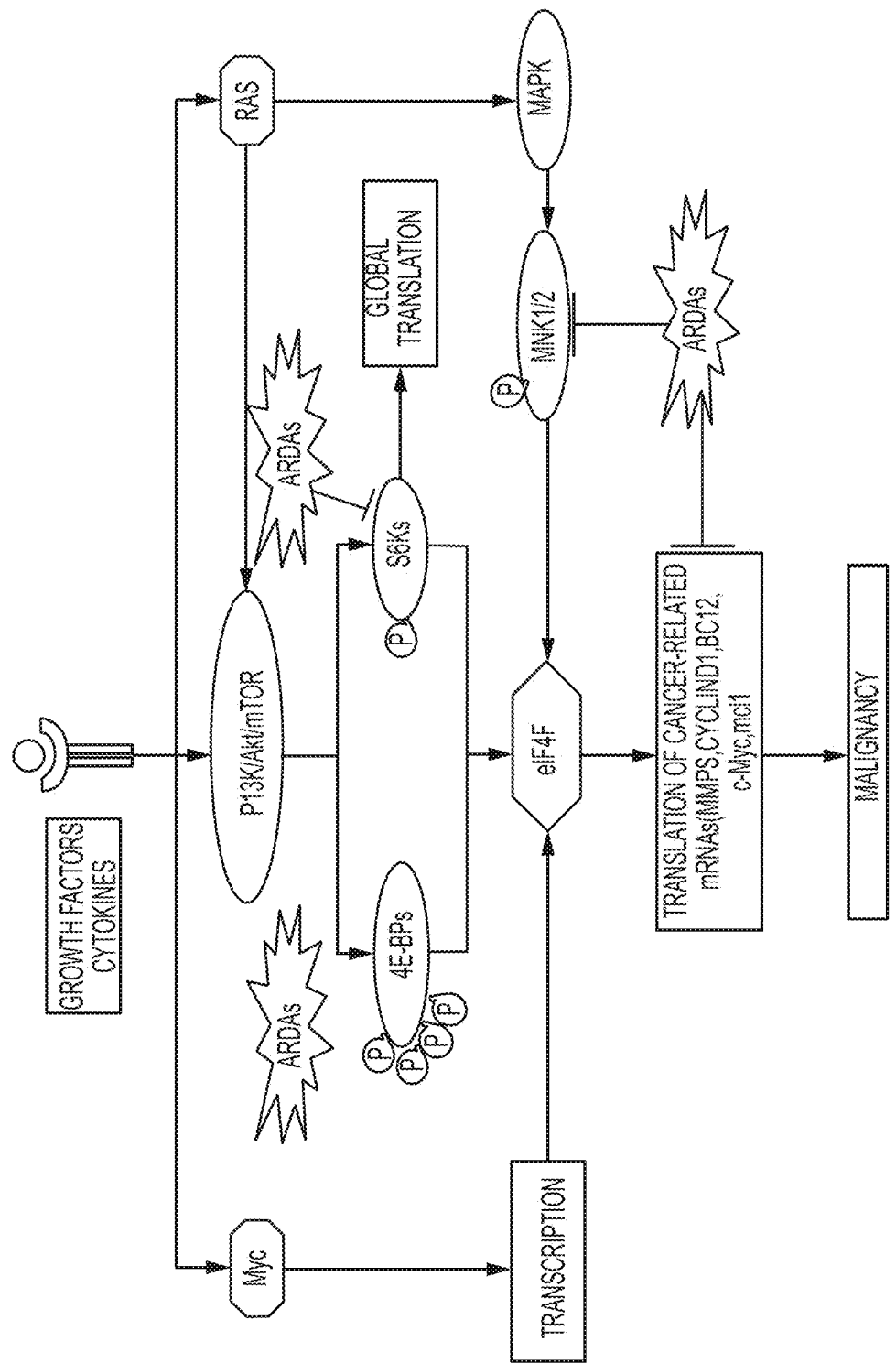
FIG. 3: Schematic representation of the effects of androgen receptor downregulating and/or degrading agents, e.g. "ARDA compounds" on the PI3K and MAPK pathways.

Galeterone (Gal) is a small-molecule, formulated for oral administration, that is currently in advanced clinical development for the treatment of castration resistant prostate cancer (CRCP). Gal disrupts androgen receptor (AR) via three distinct mechanisms of action. Recent studies show that the molecule has the ability to also effectively modulate oncogenic eukaryotic protein translation via modulation of the mitogen activating protein kinase interacting kinase (Mnk)/eIF4E pathway and also inhibition of NF-κB activation. Because AR, Mnk/eIF4E and NF-κB have been implicated as important oncogenic targets causing proliferation, metastasis and in acquired drug resistance of PDAC cells, these unique mechanisms of Gal and its improved analogs may offer an advantage over current drugs in treating PDAC. In some embodiments, ARDA compounds may affect proteasomal degradation pathways. The present invention encompasses methods of using Gal or its analogs, especially, VNPP414 and VNPP433-3β, to inhibit PDAC cell proliferation, colonization, invasion and migration and also induce apoptosis. The agents also sensitize gemcitabine resistant cells and synergistically enhance the efficacy of gemcitabine. These effects may be associated with attenuation of Mnk1/2-eIF4E pathway, NF-κB(p-p65) and metastasis markers (N-cadherin, E-cadherin and EZH2) (FIGS. 1, 2 and 3).

The lead androgen receptor downregulating and/or degrading agents, e.g., "ARDA compounds" (VN/124-1 (galeterone), VNPP414 and VNPP433-3β), may show to be therapeutically efficacious and safe in clinically relevant pancreatic cancer cell models. By developing drug-like small molecules that are efficacious against several forms of PDAC, including drug-resistant PDAC, new agents that may treat this deadly disease have been identified.

Androgen Receptor

Several common cancers and diseases are associated with androgen signaling, such as, for example, prostate cancer, breast cancer, ovarian cancer, bladder cancer, pancreatic cancer and polycystic ovary disease.

Figure 5:
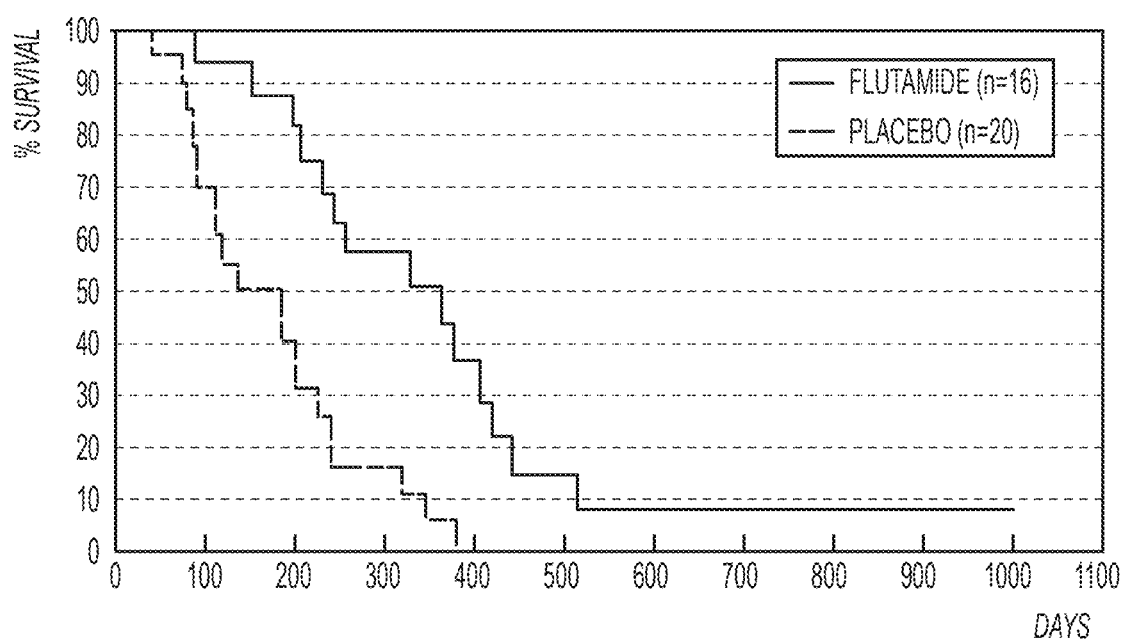
FIG. 5: Survival time of patients with pancreatic cancer who received over 6-weeks treatment with Flutamide (250 mg, three times daily) (23).

Another important oncogenic target present in a sub-set of PDAC is the androgen receptor (AR), which resulted in small Phase II clinical trials in PDAC patients in which the anti-androgen/AR blocker, flutamide (Drogenil®), doubled survival duration over control patients (FIG. 5) (23). Animal and human studies with analogues of luteinizing releasing hormone, which reduce serum testosterone concentrations, have shown promising effects in inhibiting tumor growth. A recent study demonstrated the involvement of AR and interleukin-6 (IL-6) signaling in pancreatic cancer (4). Specifically, IL-6 was shown to enhance pancreatic cancer cell migration in the presence of AR and this activity was blocked by AR-siRNA (4).

The present disclosure, among other things, provides the insight that, given that most of the early studies were specifically directed at the role of androgen modulation of AR in PDAC, the fact that non-androgenic factors, such as IL-6 (which is elevated in patients with pancreatic tumors) (27, 28), can regulate AR suggests that an androgen-independent regulation of the AR in PDAC is a viable pathway worthy of investigation. Indeed, the present disclosure, without wishing to be bound by any particular theory, provides the insight that ARDAs capable of downregulating and/or degrading several forms of AR and also blocking AR transactivation may be able to provide an approach to the treatment of PDAC. Nuclear receptors such as AR can also integrate diverse signaling cascades (e.g., RAS, PI3K, etc.). Consequently, a ligand-independent signaling pathway may lead to inappropriate activation of ARs in PDAC tumors contributing to growth of survival and metastasis of the tumor (28).

Mutations and amplification of AR, alterations in protein kinases, growth factors and nuclear receptor coactivators have all been proposed to modulate AR signaling. Mutations in the ligand binding domain of AR are shown to broaden the ligand binding profile of the mutant receptor. Increased AR expression level is shown to associate with the development of resistance to anti-androgen therapy (McPhaul, M. J. et al., J Investig. Dermatol Symp Proc 8, 1-5 (2003)). Several AR splice variants (AR3, AR4, AR4b, AR5 and AR8) have been identified. All the variants contain the intact N-terminal transactivation domain and the DNA binding domain, but lack the ligand binding domain, and therefore, are true androgen-independent. AR3 is constitutively active and its transcriptional activity may not be regulated by androgens or antiandrogens. AR3 may play a distinct role in ablation-independent growth through the regulation of a unique set of genes, including AKT1, which are not regulated by the prototype AR.

Hormone therapy typically utilizes one or more of LHRH agonists (Lupron, eligard, goserelin, tripterelin, histrelin) and/or LHRH antagonists (firmagon). Hormone therapy may be used in conjunction with surgical resection of the tumor, orchietomy (surgical castration), or radiation therapy or radiopharmaceutical (Radium 223 Dichloride, Xofigo (Radium 223 Dichloride).

Anti-androgen therapy inhibits the androgen receptor. Examples include abiraterone, flutamide, bicalutamide, nilutamide, ARN-509 and enzalutamide. Drugs have been developed to target the androgen receptor signaling pathway, and agents utilized in such strategies include certain CYP17 inhibitors or modulators, antiandrogens, chaperone inhibitors (targeting heat shock proteins, Hsp-27 inhibitor), androgen-receptor modulator (blocking transactivation domain of the receptor).

Mnl-eIF4E

The present disclosure demonstrates that certain ARDAs effectively target oncogenic eukaryotic protein translation, via modulation of Mnk-eIF4E axis. These targets have been implicated in the development, progression, metastasis and drug resistance of PDAC (2-5). In addition, without wishing to be bound by any particular theory, the present disclosure proposes that, by targeting Mnk-eIF4E which is downstream of KRAS oncogene, the action of KRAS could effectively be suppressed for the first time. It is worth noting that Mnk/p-eIF4E inhibition induces chemo-sensitization in cancer cells (2, 19).

Advances in PDAC molecular biology clearly demonstrate that K-RAS is the most frequently (90%) mutated oncogene in pancreatic tumors and the key driver of the disease (6). The K-RAS oncogene constitutively activates the MAPK pathway as well as the PI3k-Akt-mTOR pathway, which are known to promote growth and development of PDAC (9, 10). These two signaling pathways converge downstream at the eukaryotic translational initiation complex eIF4F which mediates cap-dependent mRNA translational initiation apparatus critical for eukaryotic protein synthesis (11-13) (FIG. 1). The PI3K-Akt-mTORC1 pathway, which is frequently activated in human cancers, releases 4E-BPs from eIF4E, and permits eIF4E to bind eIF4G, which, in turn, assembles the eIF4F complex comprising eIF4E, eIF4G, eIF4A, and eIF3. Mnk1 and Mnk2, which are activated by Erk and by the stress inducible kinase p38, use eIF4G as a docking site to phosphorylate efficiently eIF4E. The phosphorylation of eIF4E may be necessary for its oncogenic activity, probably through the differential translation of proteins that are required for oncogenesis. (FIG. 1). In addition, without wishing to be bound by any particular theory, the present disclosure encompasses the insight that phosphorylation of eIF4E by Mnk1/2 provides a new avenue for cancer therapy, and furthermore that inhibition of eIF4E phosphorylation could have similar consequences as the inhibition mTORC1 by rapalogs, but with the advantage that it does not elicit the activation of Akt as a result of the inhibition of the negative feedback loops mediated by mTORC1.

Protein Translation and PDAC

The present invention utilizes protein translation in promoting drug resistance and metastasis phenotype in PDAC. Presented here are certain ARDA drugs that specifically inhibit protein translation-driven PDAC in clinically relevant PDAC models alone and in combination with current PDAC FDA-approved drugs, such as gemcitabine and erlotinib (29).

Mammalian Target of Rapamaycin (mTOR) via the 4E-BP1 binding protein modulates the eIF4E, the core (rate-limiting) component of eIF4F complex (14). An additional layer of regulation of eIF4E is provided by its phosphorylation in serine 209 by the MAPK interacting kinases Mnk1 and Mnk2 (15, 16). Furthermore, overexpression of Mnk1/2 and eIF4E phosphorylation is a vital oncogenic occurrence that enhances selective translation of "weak" mRNAs, many of which encode malignancy-related genes that are involved in cell growth (cMyc, CDK2, cyclin Dl), cell survival evasion of apoptosis (Mcl-1, Bcl-2, survivin), metastasis (MMP9, heparanase) or angiogenesis (VEGF, FGF2) (17, 18). Activation and overexpression of the Mnk-eIF4E pathway is implicated in the development and progression of PDAC and to gemcitabine-induced resistance (2, 19).

Figure 4:
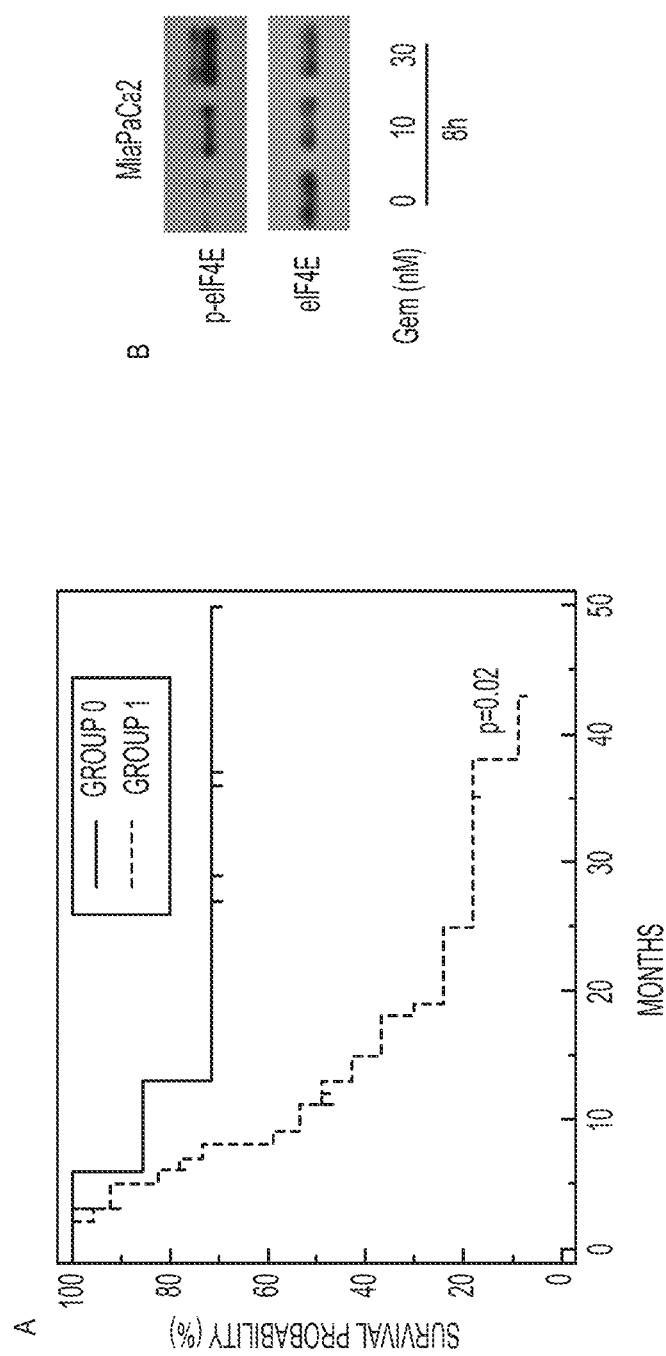
FIG. 4.

Indeed, in a study by Adesso and colleagues (2), screening of a cohort of PDAC patients by immunocytochemistry showed that eIF4E phosphorylation correlated with disease grade, early onset of disease and worse prognosis (FIG. 4). This study also demonstrated that gemcitabine triggers a pro-survival response in PDAC cells through activation of Mnk-2/eIF4E pathway (2). In addition, Baylot and colleagues (19) reported that gemcitabine resistance in MiaPaCa-2 PDAC cells involved up-regulation of eIF4E.

A rationale for inhibiting Mnks in certain cancer cells (specifically, prostate and/or lymphoma) to disrupt Mnk-eIF4E pathway as a viable therapeutic target is elegantly described in two back-to-back papers published in PNAS (20, 21). In summary, these two elegant studies clearly demonstrate that the use of mice carrying a non phosphorylatable mutant eIF4E (20) or lacking both Mnk1 and Mnk2 kinases (21) revealed that the phosphorylation of eIF4E contributes to cell transformation and tumor development. Thus, Mnk1/2 kinases are dispensable for development and survival in mammalian models (20-22), making them potentially attractive as therapeutic targets for cancer. In addition, these findings clearly raise the possibility that chemical compounds that prevent the phosphorylation of eIF4E could act as anticancer drugs.

Galeterone (Gal), a 17α-hydroxylase/17,20-lyase inhibitor and its analogs, have exhibited additional effects on the androgen receptor (AR) and the oncogenic translational machinery. These small molecule inhibitors significantly depleted Mnk1/2 protein expression and decreased eIF4E phosphorylation. Interestingly, our studies revealed that the phosphorylation level of NF-κB (p65) was significantly decreased after exposing pancreatic cancer cells to ARDAs. These targets are implicated in PDAC progression and drug resistance.

No other currently approved drugs effectively target protein translation, however, Galeterone (VN/124-1) and its new analogs have the potential to be an advancement in the treatment of many forms of pancreatic cancer and potentially other cancers and diseases that are driven by protein translation. In addition, the inactivation of these critical oncogenic pathways can lead to sensitization of PDAC cells to current PDAC conventional therapeutic agents, such as Gemcitabine.

ARDA Compounds

The present disclosure relates, in some embodiments, to therapeutic regimens for treating pancreatic cancer with a so-called androgen receptor downregulating and/or degrading agents, e.g. "ARDA compounds." As used, herein, the term "ARDA compound" refers either to a compound of formula (I), as described herein, or any of the compounds provided in either of international PCT publications WO 2014/153,215 or WO 2014/165,815, each of which is incorporated herein by reference.

In some embodiments, the ARDA compound is any of the compounds provided in international PCT publication WO 2014/153,215.

In some embodiments, the ARDA compound is any of the compounds provided in international PCT publication WO 2014/165,815.

In some embodiments, the ARDA compound is of formula (I)

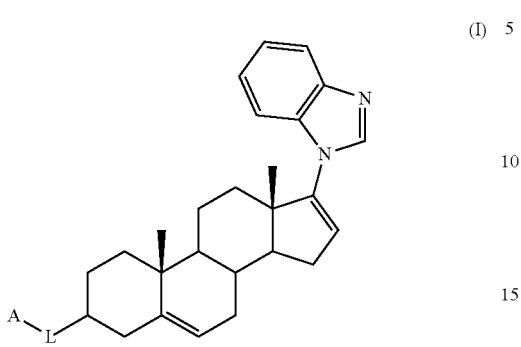

(I)

or a pharmaceutically acceptable salt thereof,
wherein

L is a covalent bond or a bivalent, straight or branched, optionally substituted $C_1$-$C_4$ alkylene; and A is —OH, —OC(O)CH$_3$, imidazolyl or pyridyl, wherein the imidazolyl or pyridyl is optionally substituted with —$C_1$-$C_4$ alkyl, —O$C_1$-$C_4$ alkyl and/or -halogen.

As used herein, the term "$C_1$-$C_4$ alkylene" refers to a bivalent alkylene chain, i.e., a polymethylene group, —(CH$_2$)$_n$—, wherein n is from 1 to 4.

In some embodiments, L is a covalent bond. In some embodiments, L is a covalent bond and A is —OH or —OC(O)CH$_3$.

In some embodiments, L is substituted $C_1$-$C_4$ alkylene. In some embodiments, L is unsubstituted $C_1$-$C_4$ alkylene. In some embodiments, L is branched $C_1$-$C_4$ alkylene. In some embodiments, L is straight $C_1$-$C_4$ alkylene. In some embodiments, L is —CH$_2$—. In some embodiments, L is —CH$_2$CH$_2$—. In some embodiments, L is —CH$_2$CH$_2$CH$_2$—. In some embodiments, L is —CH$_2$CH$_2$CH$_2$CH$_2$—. In some embodiments, L is $C_1$-$C_4$ alkylene substituted with oxo (=O). In some embodiments, L is —C(O)—. In some embodiments, L is $C_1$-$C_4$ alkylene wherein at least one methylene unit of L is replaced by one or more of —NR—, —O—, —C(O)—, —C(O)O—, —OC(O)—, —NRC(O)—, —C(O)NR—, —N(R)SO$_2$—, or —SO$_2$N(R)—, wherein R is H or $C_1$-$C_4$ alkyl. Exemplary $C_1$-$C_4$ alkyl groups are methyl, ethyl, propyl, isopropyl, butyl, isobutyl, and tert-butyl. In some embodiments, R is H. In some embodiments, R is methyl.

In some embodiments, L is —C(O)O—. In some embodiments, L is —OC(O). In some embodiments, L is —CH$_2$O—. In some embodiments, L is —OCH$_2$—. In some embodiments, L is —C(O)NH—. In some embodiments, L is —NHC(O)—. In some embodiments, L is —SO$_2$NH—. In some embodiments, L is —NHSO$_2$—.

In some embodiments, A is unsubstituted. In some embodiments, A is substituted. Exemplary substituted groups include —$C_1$-$C_4$ alkyl, —O$C_1$-$C_4$ alkyl, or -halogen (i.e., —F, —Br, —Cl or —I). In some embodiments, A is substituted with one or more methyl groups. In some embodiments, A is substituted with one or more halogen atoms.

In some embodiments, A is

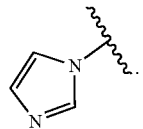 [SMILES: *n1ccnc1]

In some embodiments, A is

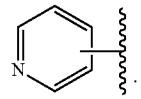

In some embodiments, A is

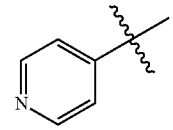

In some embodiments, A is

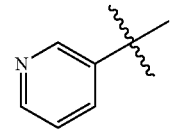

In some embodiments, A is

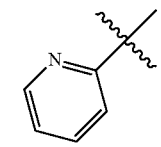

In some embodiments, the ARDA compound of formula (I) is
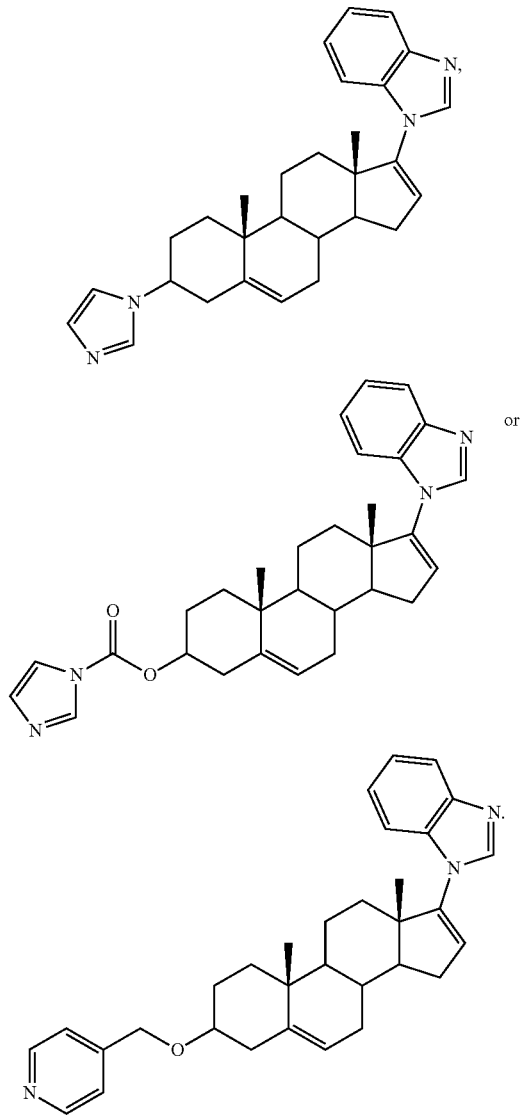 or
In some embodiments, the ARDA compound of formula (I) is
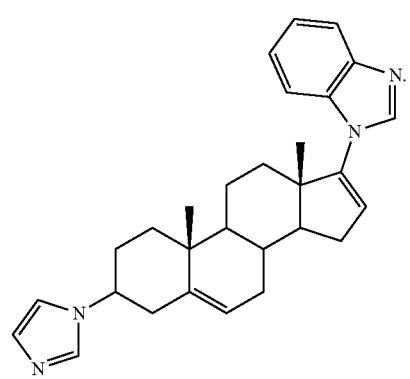 [SMILES: C[C@]12CCC(n3ccnc3)CC1=CCC1C2CC[C@]2(C)C(n3cnc4ccccc43)=CCC12]
In some embodiments, the ARDA compound of formula (I) is
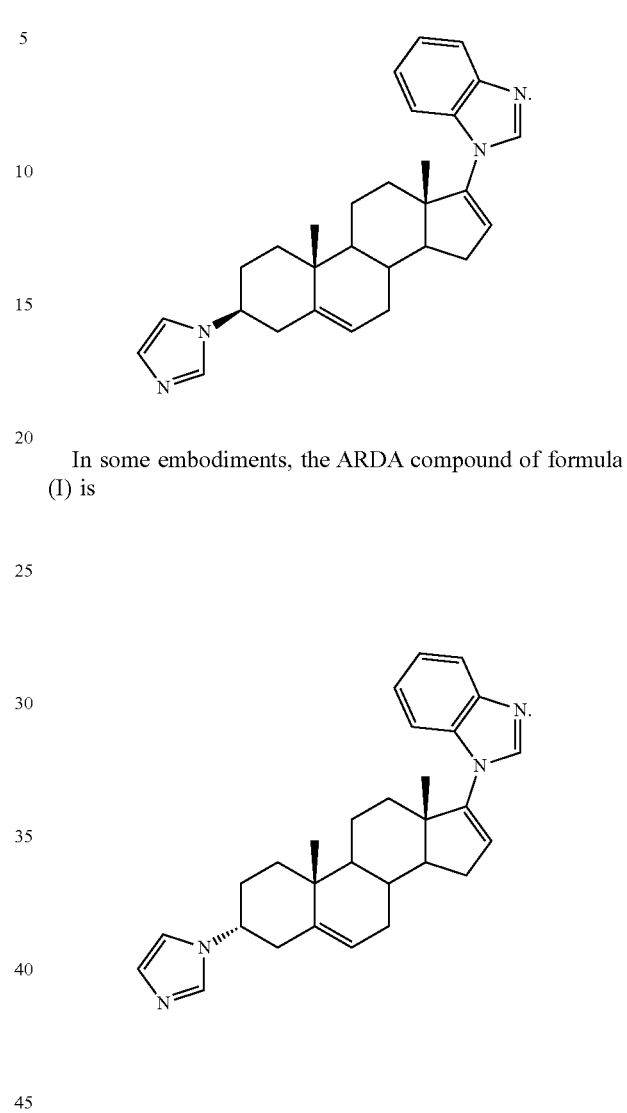
In some embodiments, the ARDA compound of formula (I) is
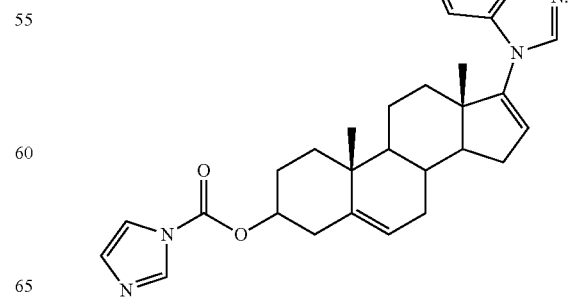

In some embodiments, the ARDA compound of formula (I) is

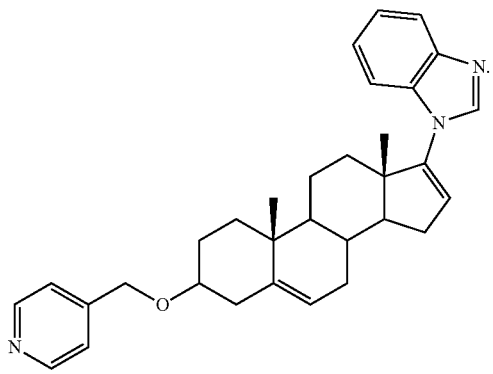 [SMILES: C[C@]12CCC(OCc3ccncc3)CC1=CCC1C2CC[C@]2(C)C(n3cnc4ccccc43)=CCC12]

Galeterone

In some embodiments, the ARDA compound is of formula (I) wherein L is a covalent bond and A is OH (i.e., the ARDA compound is "galeterone.") Galeterone (VN/124-1) is a compound being developed for the treatment of androgen-sensitive cancers. Without being bound by theory, galeterone is thought to inhibit AR activity via at least three distinct mechanisms of action. Galeterone has been shown to be a potent inhibitor of CYP17 lyase in the steroidogenic pathway, to antagonize binding of androgens and to the androgen receptor, and to downregulate and/or degrade the androgen receptor. A net effect on androgen signaling pathway includes an inhibition of prostate cancer growth. (See U.S. Pat. No. 7,875,599, incorporated herein by reference.)

As noted, galeterone is a selective agent that disrupts androgen signaling at multiple points in the pathway. Galeterone has a chemical structure as set forth in the formula:

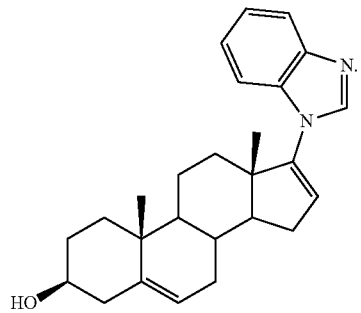 [SMILES: C[C@]12CC[C@H](O)CC1=CCC1C2CC[C@]2(C)C(n3cnc4ccccc43)=CCC12]

In some embodiments, methods described herein relate to a "galeterone composition" that includes galeterone in the form of a pharmaceutically acceptable salt of the compound depicted above (i.e., galeterone).

In some embodiments, methods described herein relate to an ARDA compound that is a compound of formula (I) wherein L is a covalent bond and A is —OC(O)CH$_3$, corresponding to an acetate prodrug of galeterone of formula:

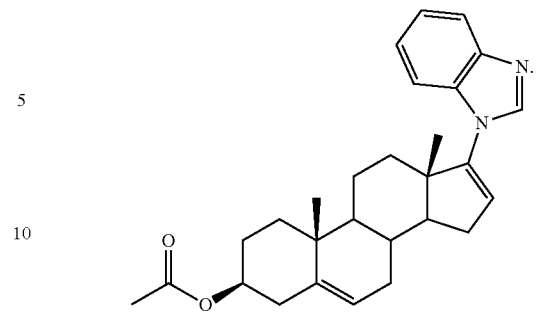

In some embodiments, the pharmaceutically acceptable salt of galeterone, or of the acetate prodrug of galeterone, is the hydrochloride salt or acetic acid salt.

Therapeutic Regimens

Markers and Characterization

In some embodiments, technologies provided by the present disclosure involve assessment of type of cancer from which a patient is suffering. In some embodiments, a patient is suffering from pancreatic cancer. In some embodiments, a patient is suffering from pancreatic ductal adenocarcinoma (PDAC).

In general, the present disclosure provides technologies according to which one or more markers or characteristics of a subject is analyzed and/or assessed; in some embodiments, a therapeutic decision is made based on such analysis and/or assessment.

In some embodiments, a marker is an agent or entity whose presence, form and/or level is correlated in a relevant population with a relevant feature (e.g., type or stage of cancer). In some embodiments, the present disclosure contemplates identification, classification, and/or characterization of one or more biomarkers relevant for the treatment of pancreatic cancer with an ARDA as described herein.

In some embodiments, classification of a patient as suffering from a particular type of cancer may involve assessment of stage of cancer. In some embodiments, classification of a patient as suffering from a particular type of cancer may involve assessment of disease burden in the patient (e.g. the number of cancer cells, the size of a tumor, and/or amount of cancer in the body). In some particular embodiments, classification of a patient as suffering from a particular type of cancer may involve assessment of the extent or number of circulating tumor cells (CTC).

In general, type of cancer may be assessed in accordance with the present invention via any appropriate assay, as will be readily appreciated by those of ordinary skill in the art. A variety of assays for cancer type are known in the art including, for example, those that utilize histological assessment (e.g., of a biopsy sample), imaging (e.g., magnetic resonance imaging (MRI), positron emission tomography (PET), computed tomography (CT) ultrasound, endoscopy, x-rays (e.g., mammogram, barium swallow, panorex), ductogram, or bone scan.

In some embodiments, a galeterone therapy comprises assessing a level of one or more biomarkers indicative of a stage or a form of pancreatic cancer. In some embodiments, a galeterone therapy comprises assessing a level of one or more biomarkers selected from a steroidogenic pathway marker, AR splice variant, marker of resistance and marker of metastatic disease. In some embodiments, a galeterone therapy comprises assessing the level and/or activity of matrix metalloproteinases (e.g. MMP9). In some embodiments, a galeterone therapy comprises assessing the level of EZH2.

In some embodiments, ARDA compound therapy comprises assessing a level of one or more biomarkers indicative of pancreatic diagnosis, staging, therapeutic efficacy outcome, or disease progression. In some embodiments, ARDA compound therapy includes assessment if outcome determinants are associated with aryl hydrocarbon receptor (AhR or AHR or ahr or ahR). In some embodiments, ARDA compound therapy includes assessment if outcome determinants are associated with microRNAs, e.g miR-10 b, MIR-155, miR-106b, miR100, miR-99b, miR-99a, miR-32f-3p42f-3, miR-126, miR130a. In some embodiments, a galeterone therapy comprises assessing a level of one or more biomarkers selected from the eIF4E-Mnk1/2 axis. In some embodiments, a galeterone therapy comprises assessing the level of eIF4E. In some embodiments, a galeterone therapy comprises assessing the level of phosphorylation of eIF4E. In some embodiments, a galeterone therapy comprises assessing the level of eIF4G. In some embodiments, a galeterone therapy comprises assessing the level of eIF4A. In some embodiments, a galeterone therapy comprises assessing the level of eIF3. In some embodiments, a galeterone therapy comprises assessing the level Mnk1 and/or Mnk2. In some embodiments, a galeterone therapy comprises assessing the level Erk and/or inducible kinase p38.

In some embodiments, AR splice variants can serve as predictive and/or prognostic markers (biomarkers) to determine the degree of the disease and predict outcome in response to hormonal therapy. In other embodiments, these novel androgen receptor splice variants represent targets for therapeutics/drugs which can be used to treat human subjects diagnosed with pancreatic cancer.

In some embodiments, the invention is directed to methods of treating or preventing pancreatic cancer in a patient, comprising administering to the patient in need thereof an effective amount of an agent that inhibits the function of an androgen receptor splice variant selected from the group consisting of AR3, AR4, AR4b, AR5 and AR8. In some embodiments, ARDA compounds may be compounds that affect proteasomal degradation pathways.

Patient Populations

In some embodiments, a patient population includes one or more subjects suffering from cancer. In some embodiments, a patient population includes one or more subjects suffering from metastatic disease.

In some embodiments, a patient population includes one or more subjects (e.g., comprises or consists of subjects) suffering from an androgen dependent disease, disorder or condition, selected from the group consisting of diseases disorders or conditions that are characterized or marked by excessive production of adrenal or gonadal androgens; adrenal adenomas, carcinomas, or hyperplasia; Leydig cell tumors in men; arrhenoblastomas and polycystic ovarian syndrome in women; and combinations thereof. In some embodiments, an androgen dependent disease disorder or condition may be or comprise Kennedy's disease, breast cancer, prostate cancer, bladder cancer, pancreatic cancer, ovarian cancer, acne, hidradenitis suppruartiva, androgenic alopecia, keratosis pilaris, begin prostatic hyperplasia, hirsutism, or any combination thereof. In some embodiments, an androgen-dependent disease, disorder or condition is or comprises pancreatic cancer, which, in some embodiments, may be associated with increased levels of androgen receptor compared to a reference.

In some preferred embodiments, a patient population includes one or more subjects suffering from pancreatic cancer. In some embodiments, a patient population includes one or more subjects suffering from pancreatic adenocarcinoma. In some embodiments, a patient population includes one or more subjects suffering from pancreatic invasive adenocarcinoma. In some embodiments, a patient population includes one or more subjects suffering from pancreatic ductal adenocarcinoma. In some embodiments, a patient population includes one or more subjects suffering from increased growth of cells in the pancreas. In some embodiments, a patient population includes one or more subjects suffering from non-adenocarcinomas. In some embodiments, a patient population includes one or more subjects suffering from neuroendocrine tumors, which can arise from the hormone-producing cells of the pancreas.

In some embodiments, a patient population includes one or more subjects suffering from exocrine cancers. In some embodiments, a patient population includes one or more subjects suffering from acinar cell carcinoma of the pancreas. In some embodiments, a patient population includes one or more subjects suffering from cystadenocarcinoma. In some embodiments, a patient population includes one or more subjects suffering from pancreatoblastoma. In some embodiments, a patient population includes one or more subjects suffering from adenosquamous carcinomas, signet ring cell carcinomas, hepatoid carcinomas, colloid carcinomas, undifferentiated carcinomas, and undifferentiated carcinomas with osteoclast-like giant cells. In some embodiments, a patient population includes one or more subjects suffering from solid pseudopapillary tumor.

In some embodiments, a patient population includes one or more subjects (e.g., comprises or consists of subjects) who received previous therapy for treatment of cancer (e.g., pancreatic cancer). In some embodiments, a patient population includes one or more subjects (e.g., comprises or consists of subjects) who have not received previous therapy for treatment of cancer (e.g., pancreatic cancer). In some embodiments, a patient population consists of patients who have not received previous therapy for treatment of pancreatic cancer.

In some embodiments, a patient who received previous therapy may have received previous therapy selected from the group consisting of chemotherapy, immunotherapy, radiation therapy, palliative care, surgery, Whipple procedure, and combinations thereof.

In some embodiments, a patient population includes one or more subjects (e.g., comprises or consists of subjects) suffering from an anti-androgen resistant disease. For example, in some embodiments, a patient population suffering from anti-androgen resistant disease may have previously been treated with an antiandrogen therapy, treatment with an androgen receptor antagonist, or a combination thereof. In some embodiments, some or all patients may have disease that initially responded to the anti-androgen therapy, but subsequently became insensitive to the therapy (e.g., worsened despite continued anti-androgen treatment). In some embodiments, some or all patients may have disease that was always insensitive to antiandrogen therapy and/or may not have previously received anti-androgen therapy.

In some embodiments, a patient population includes one or more subjects (e.g., comprises or consists of subjects) who have received and/or are receiving other therapy, e.g., so that the galeterone composition is administered in combination with the other therapy (e.g. chemotherapy agents and/or agents listed in Example 19. In some embodiments, such other therapy may comprise or consist of therapy for cancer (e.g., as described herein), pain, nausea, constipation, for treatment of one or more side effects (e.g., pruritis, hair loss, sleeplessness, etc) associated with cancer therapy, etc, or any combination thereof. In some embodiments, galeterone therapy as described herein is not administered in combination with an agent whose proper metabolism relies on CYP17 activity (given that galeterone inhibits CYP17).

The present invention provides a method of treating pancreatic cancer, which comprises treating a patient identified as having pancreatic cancer, with a therapeutically effective amount of galeterone or a pharmaceutically acceptable salt thereof.

In some embodiments, the present invention provides a method of preventing or delaying the onset of pancreatic cancer, comprising administering to a patient identified to be in need of prevention, or delaying the onset, of pancreatic cancer a prophylatically effective amount galeterone or a pharmaceutically acceptable salt thereof.

In some embodiments, the invention provides a method for treating a patient for pancreatic cancer (e.g., pancreatic ductal adenocarcinoma) previously treated with a treatment regimen comprising gemcitabine and/or erlotinib by administering to such a patient a therapeutically effective amount of galeterone or a pharmaceutically acceptable salt thereof.

In some embodiments, the invention provides a method for treating a patient for pancreatic cancer (e.g., pancreatic ductal adenocarcinoma) previously treated with a treatment regimen comprising chemotherapy by administering to such a patient a therapeutically effective amount of galeterone or a pharmaceutically acceptable salt thereof.

The present invention further provides use of a compound (e.g., galeterone) or a pharmaceutically acceptable salt thereof for the manufacture of a medicament useful for treating, preventing or delaying the onset of pancreatic cancer, or treating, preventing or delaying the onset of pancreatic cancer refractory (e.g., resistant) to gemcitabine and/or erlotinib.

In some embodiments, the patient is suffering from pancreatic cancer that is resistant to other therapies (e.g., chemotherapy, therapies listed in Example 19, radiation, surgery, etc.). In some embodiments, the patient is suffering from pancreatic cancer that is gemcitabine resistant. In some embodiments, the patient is suffering from pancreatic ductal adenocarcinoma that is gemcitabine resistant. In some embodiments, the patient is suffering from pancreatic cancer that is naïve to other therapies. In some embodiments, the patient is suffering from pancreatic ductal adenocarcinoma that is gemcitabine naïve. In some embodiments, the patient is suffering from pancreatic ductal adenocarcinoma that is gemcitabine and/or erlotinib resistant. In some embodiments, the patient is suffering from pancreatic cancer that is androgen dependent. In some embodiments, the patient is suffering from pancreatic cancer that is androgen independent.

Dosing Regimens

In general, each active agent (e.g., galeterone) for use in accordance with the present invention is formulated, dosed, and administered in therapeutically effective amount using pharmaceutical compositions and dosing regimens that are consistently with good medical practice and appropriate for the relevant agent(s) and subject. In principle, therapeutic compositions can be administered by any appropriate method known in the art, including, without limitation, oral, mucosal, by-inhalation, topical, buccal, nasal, rectal, or parenteral (e.g. intravenous, infusion, intratumoral, intranodal, subcutaneous, intraperitoneal, intramuscular, intradermal, transdermal, or other kinds of administration).

In some embodiments, a dosing regimen for a particular active agent may involve intermittent or continuous administration, for example to achieve a particular desired pharmacokinetic profile or other pattern of exposure in one or more tissues or fluids of interest in the subject receiving therapy.

In some embodiments, different agents administered in combination may be administered via different routes of delivery and/or according to different schedules. Alternatively or additionally, in some embodiments, one or more doses of a first active agent is administered substantially simultaneously with, and in some embodiments via a common route and/or as part of a single composition with, one or more other active agents.

Factors to be considered when optimizing routes and/or dosing schedule for a given therapeutic regimen may include, for example, the particular indication being treated, the clinical condition of a subject (e.g., age, overall health, prior therapy received and/or response thereto, etc) the site of delivery of the agent, the nature of the agent, the mode and/or route of administration of the agent, the presence or absence of combination therapy, and other factors known to medical practitioners. For example, in the treatment of cancer, relevant features of the indication being treated may include, among other things, one or more of cancer type, stage, location, etc.

In some embodiments, one or more features of a particular pharmaceutical composition and/or of a utilized dosing regimen may be modified over time (e.g., increasing or decreasing amount of active in any individual dose, increasing or decreasing time intervals between doses, etc), for example in order to optimize a desired therapeutic effect or response.

In general, type, amount, and frequency of dosing of active agents in accordance with the present invention are governed by safety and efficacy requirements that apply when relevant agent(s) is/are administered to a mammal, preferably a human. In general, such features of dosing are selected to provide a particular, and typically detectable, therapeutic response as compared with what is observed absent therapy.

In context of the present invention, an exemplary desirable therapeutic response may involve, but is not limited to, inhibition of and/or decreased tumor growth, tumor size, metastasis, one or more of the symptoms and side effects that are associated with a tumor, as well as increased apoptosis of tumor cells, therapeutically relevant decrease or increase of one or more cell marker or circulating markers and the like. Such criteria can be readily assessed by any of a variety of immunological, cytological, and other methods that are disclosed in the literature.

In some embodiments, it may be desirable to tailor dosing regimens, and particularly to design sequential dosing regimens, based on timing and/or threshold expression levels of inducible markers, whether for particular types of tumors, particular tumors, particular patient populations (e.g., carrying genetic markers), and/or particular patients. In some such embodiments, therapeutic dosing regimens may be combined with or adjusted in light of detection methods that assess expression of one or more inducible markers prior to and/or during therapy.

Formulations

A pharmaceutical composition, as used herein, refers to a mixture of a compound, such as galeterone, with other chemical components, such as carriers, stabilizers, diluents, dispersing agents, suspending agents, thickening agents, and/or excipients. The pharmaceutical composition facilitates administration of the compound to an organism. Pharmaceutical composition containing a compound be administered in therapeutically effective amounts as pharmaceutical compositions by any conventional form and route known in the art including, but not limited to: intravenous, oral, rectal, aerosol, parenteral, ophthalmic, pulmonary, transdermal, vaginal, otic, nasal, and topical administration.

One may administer the compound in a local rather than systemic manner, for example, via injection of the compound directly into an organ, often in a depot or sustained release formulation. Furthermore, one may administer pharmaceutical composition containing a compound in a targeted drug delivery system, for example, in a liposome coated with organ-specific antibody. The liposomes will be targeted to and taken up selectively by the organ. In addition, the pharmaceutical composition containing a compound may be provided in the form of a rapid release formulation, in the form of an extended release formulation, or in the form of an intermediate release formulation. In some embodiments, the extended release formulation releases the compound for over 1 hour, over 2 hours, over 3 hours, over 4 hours, over 6 hours, over 12 hours, over 24 hours, or more. In some embodiments, the extended release formulation releases the compound at a steady rate for over 1 hour, over 2 hours, over 3 hours, over 4 hours, over 6 hours, over 12 hours, over 24 hours, or more.

For oral administration, a compound can be formulated readily by combining the active compounds with pharmaceutically acceptable carriers or excipients well known in the art. Such carriers permit the compounds described herein to be formulated as tablets, powders, pills, dragees, capsules, liquids, gels, syrups, elixirs, slurries, suspensions and the like, for oral ingestion by a subject to be treated. Generally, excipients such as fillers, disintegrants, glidants, surfactants, recrystallization inhibitors, lubricants, pigments, binders, flavoring agents, and so forth can be used for customary purposes and in typical amounts without affecting the properties of the compositions.

In some embodiments, a galeterone composition comprises galeterone or a prodrug (e.g., an acetate prodrug) of galeterone or a pharmaceutically acceptable salt thereof (i.e., of either galeterone or a acetate prodrug thereof). In some embodiments, a galeterone composition comprises galeterone or a pharmaceutically acceptable salt thereof. In some embodiments, a galeterone composition comprises a prodrug (e.g., an acetate prodrug) of galeterone or a pharmaceutically acceptable salt thereof.

In some embodiments, a pharmaceutically acceptable salt is a hydrochloride salt. In some embodiments, a pharmaceutically acceptable salt is an acetic acid salt.

In some embodiments, galeterone therapy in accordance with the present disclosure comprises administering a galeterone composition that includes active agent (e.g, galeterone, a galeterone prodrug, and/or a pharmaceutically acceptable salt of either) in non-crystalline form (e.g. amorphous). In some embodiments, a galeterone therapy comprises administering a spray-dried galeterone composition.

In some embodiments, a galeterone composition comprises polyvinylpyrrolidone (copovidone).

In some embodiments, a galeterone composition comprises active agent (e.g, galeterone, a galeterone prodrug, and/or a pharmaceutically acceptable salt of either) and copovidone in a ratio of about 1:1. In some embodiments, a galeterone composition comprises (e.g, galeterone, a galeterone prodrug, and/or a pharmaceutically acceptable salt of either) and copovidone in a ratio of about 1:2, 1:1, 2:1 or a ratio between any two of these values.

Combination Therapy

Those of ordinary skill in the art, reading the present disclosure, will readily appreciate that galeterone, as described herein, may in certain embodiments be combined with other anti-cancer therapies, including for example administration of chemotherapeutic agents, other immunomodulatory agents, radiation therapy, high-frequency ultrasound therapy, surgery, therapies listed in Example 19, FDA approved therapies for treatment of cancer, etc.

In some embodiments, galeterone is utilized in combination with one or more other therapeutic agents or modalities. In some embodiments, the one or more other therapeutic agents or modalities is also an anti-cancer agent or modality; in some embodiments the combination shows a synergistic effect in treating cancer.

Known compounds or treatments that show therapeutic efficacy in treating cancer may include, for example, one or more alkylating agents, anti-metabolites, anti-microtubule agents, topoisomerase inhibitors, cytotoxic antibiotics, angiogenesis inhibitors, immunomodulators, vaccines, cell-based therapies, organ transplantation, radiation therapy, surgery, etc. In some cases, treatments may be preventative, e.g., the Whipple procedure.

In some embodiments, galeterone (and/or other therapy with which it is combined) may be combined with one or more palliative (e.g., pain relieving, anti-nausea, anti-emesis, etc) therapies, particularly when relieves one or more symptoms known to be associated with the relevant cancer, or with another disease, disorder or condition to which a particular cancer patient is susceptible or from which the particular cancer patient is suffering.

In some embodiments, agents used in combination are administered according to a dosing regimen for which they are approved for individual use. In some embodiments, however, combination with galeterone permits another agent to be administered according to a dosing regimen that involves one or more lower and/or less frequent doses, and/or a reduced number of cycles as compared with that utilized when the agent is administered without galeterone. Alternatively or additionally, in some embodiments, an appropriate dosing regimen involves higher and/or more frequent doses, and/or an increased number of cycles as compared with that utilized when the agent is administered without galeterone.

In some embodiments, one or more doses of agents administered in combination are administered at the same time; in some such embodiments, agents may be administered in the same composition. More commonly, however, agents are administered in different compositions and/or at different times. In some embodiments, galeterone is administered sequentially and/or concurrently with other therapeutic agents (e.g., chemotherapy). In some embodiments, galeterone is administered with a chemotherapy (e.g., Gemcitabine). In some embodiments, galeterone is administered at different time intervals and concurrently with Gemcitabine. To give but one specific example, as described herein, in some embodiments, Gemcitabine is administered to a subject and then, at some period of time later, galeterone is administered with or without Gemcitabine.

EXEMPLIFICATION

Examples below were preformed using a panel of PDAC cells from primary tumors (MiaPaca-2, Panc-1, Capan-1 and HS766T), metastatic lesions (S2-013 and S2VP10) and drug-resistant MiaPaCa-GR (gemcitabine resistant-200 nM) and MiaPaCa-GTR (erlotinib-2 µM/gemcitabine-200 nM) cell lines. The activities of ARDAs and Gemcitabine (Gem) can be evaluated using complementary assays and molecular determinants can also be identified in a panel of human PDAC cells. The mechanism(s) of action of ARDAs alone and in combination with Gem with the primary goal to identify the key mediators for their activities in PDAC cells are disclosed here. Based on the results disclosed here, the most potent ARDAs were selected for mechanistic studies, alone and in combination with Gem. Initially four cell line (2 Gem-naïve and the two Gem-resistant lines) will be used. Key findings derived from these cell lines can be validated in additional cell lines if necessary. How these agents modulate Mnk1/2-peIF4E and NFκ-B can also be focused on.

Example 1: ARDAs Inhibit Cell Proliferation

Figure 6:
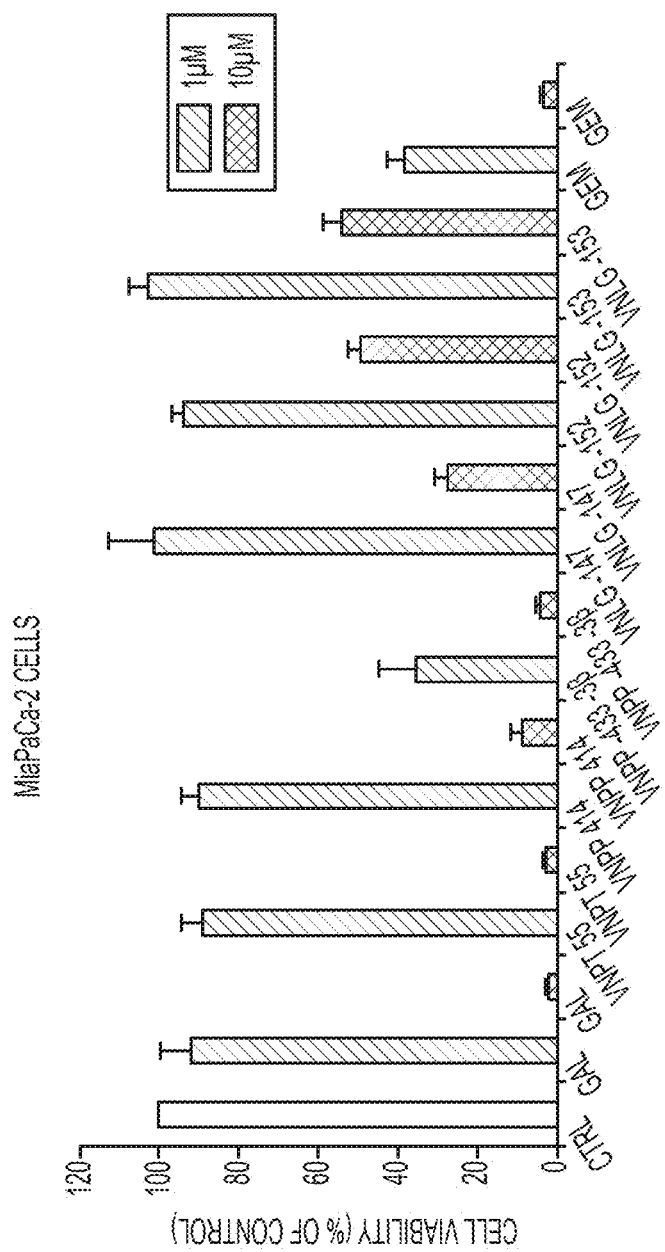
FIG. 6: Inhibition of PDAC cell proliferation: MTT assay after a 7-day agent treatment.

The present Example presents the in vitro anti-proliferative activities of compounds in three human PDAC cell lines, including, Capan-1, MiaPaCa-2 and S2-013 because of their relative resistant nature (30, 31). The cell lines used were authenticated by short tandem repeat. Representative anti-proliferative activities of these compounds in MiaPaCa-2 cells are shown in FIG. 6. The ARDAs (VN/124-1, VNPT-55, VNPP414 and VNPP433-3β) are almost as potent as gemcitabine (Gem).

Figure 7:
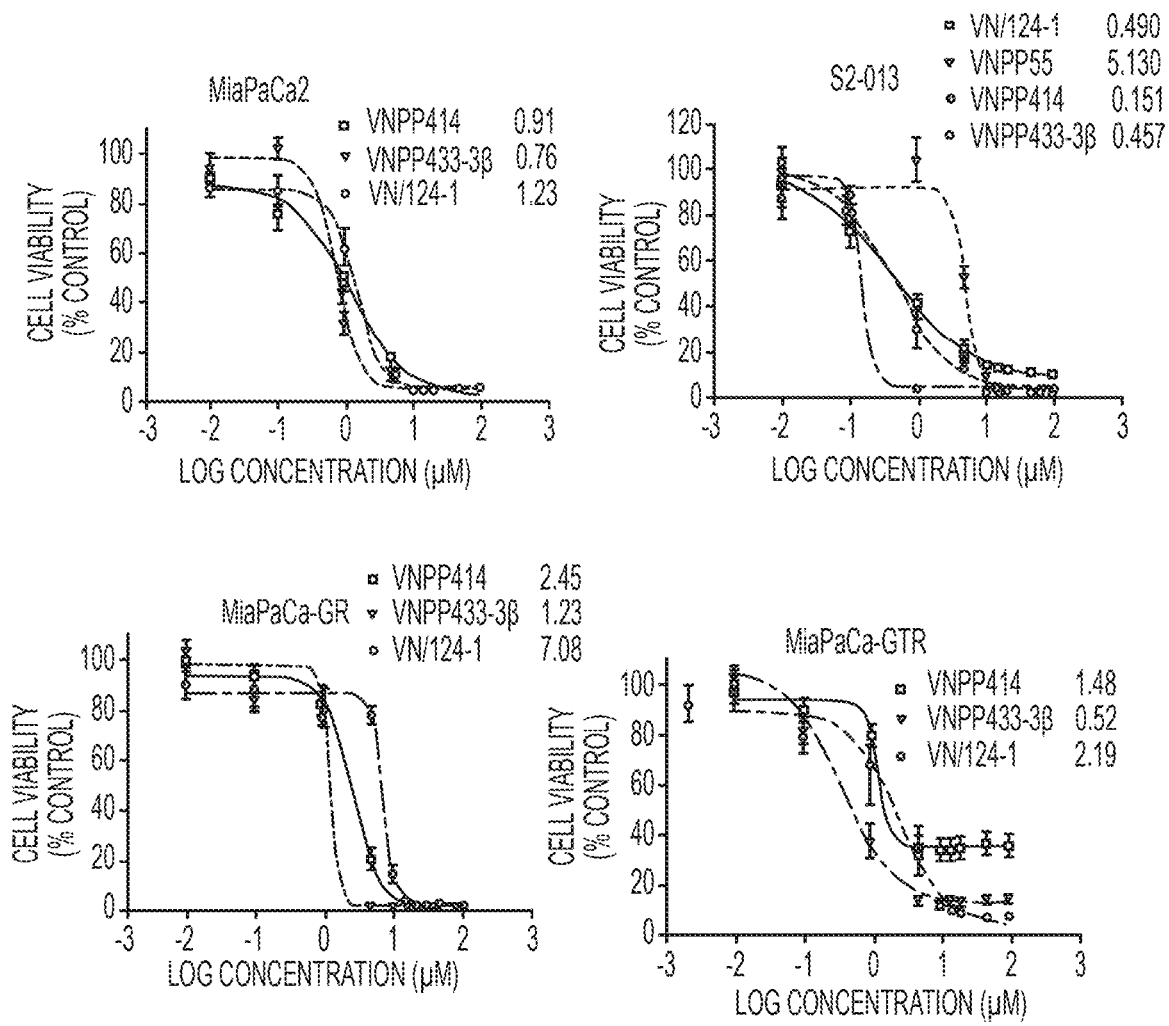
FIG. 7: Effect of Galeterone, analogs and Gemcitabine on PDAC cells. MTT cell viability assays were conducted on Gem-naïve and Gem-resistant cells.

Example 2: ARDAs Inhibit Cell Proliferation of Pancreatic & Gemcitabine-Resistant Human Pancreatic Cancer Cells The present Example investigates the potential efficacy of galeterone and three lead ARDAs in inhibiting cell viability of both gemcitabine naïve (Gem-naïve) and gemcitabine/erlotinib resistant human pancreatic cancer cells in vitro. As shown in FIG. 7, the compounds inhibit the growth of these cell lines in the mid nM to low M range. VNPP414-3β exhibited the strongest anti-proliferative activity, with $GI_{50}$ values of 0.76, 0.46, 1.23 and 0.52 µM against MiaPaCa-2, S2-013, MiaPaCa-GR and MiaPaCa-GTR, respectively. Galeterone (VN/124-1) exhibited strong anti-proliferative activity, with $GI_{50}$ values of 1.23, 0.49, 7.08 and 2.19 µM against MiaPaCa-2, S2-013, MiaPaCa-GR and MiaPaCa-GTR, respectively. Galeterone and its analogs show significant anti-proliferative active against both gemcitabine naïve and gemcitabine resistant PDAC cells.

Example 3: Determining the Mechanism of Action and Anti-Cancer Activity of ARDAs-Gemcitabine Combinations In Vitro The present Example describes studies that can be done to evaluate the anti-proliferative activities of ARDAs as single agents and in combination with gemcitabine (the elective agent in PDAC therapy). Because ARDAs described herein effectively modulate AR and diverse oncogenic signaling cascades implicated in PDAC development, progression and drug-resistance, the ARDAs could act as effective anti-PDAC agents, with the potential to inhibit tumor growth, metastasis and resistance to current PDAC FDA approved drugs (e.g., therapies listed in Example 19). An improved synthesis of the ARDAs was developed. Administration of each ARDA alone, and in combination with FDA-approved drugs, in PDAC cells and tumors was investigated as potential treatments of PDAC.

ARDAs may exhibit strong and broad synergy through direct targeting of Mnk1/2-peIF4 pathway and indirectly through targeting NF-κB. In PDAC cells, Gem triggers a pro-survival response through activation of the Mnk/eIF4E pathway (2, 19). The suppression of the Mnk/eIF4E pathway by the ARDAs disclosed here would make their combination with Gemcitabine synergistic in PDAC cells. For clarity, it is important to state here that eIFE4 is specifically phosphorylated by only Mnk1 and Mnk2.

If inhibition of Mnk1/2 are discovered to be critical for potent anti-proliferative activities and/or strong synergy with Gem, Mnk inhibitors (such as CGP57380 or cercosporamide) can be employed to further confirm their significance in single-agent and combination actions (54). The depletion of Mnk1/2 with consequent depletion of peIF4E may play key role in the efficacy of ARDAs and combination with Gem against PDAC cell lines.

The anti-tumor activity of VN/124-1, VNPP414 and VNPP433-3β, as single agents and in combination with gem in complementary in vitro models of PDAC can be characterized and their underlying mechanism of actions can be determined.

Example 4: Activity of ARDAs and Gemcitabine Alone and in Combination

The present Example investigates whether ARDAs enhance the effects of gemcitabine (Gem) in MiaPaCa-2-GTR (Gem-200 nM/tarceva(erlotinib)-5 µM resistant) PDAC cells. Cells were treated with various concentrations of ARDAs, CGP57380 (CGP, Mnk1/2 inhibitor) and Gem alone and in combination.

Figure 8:
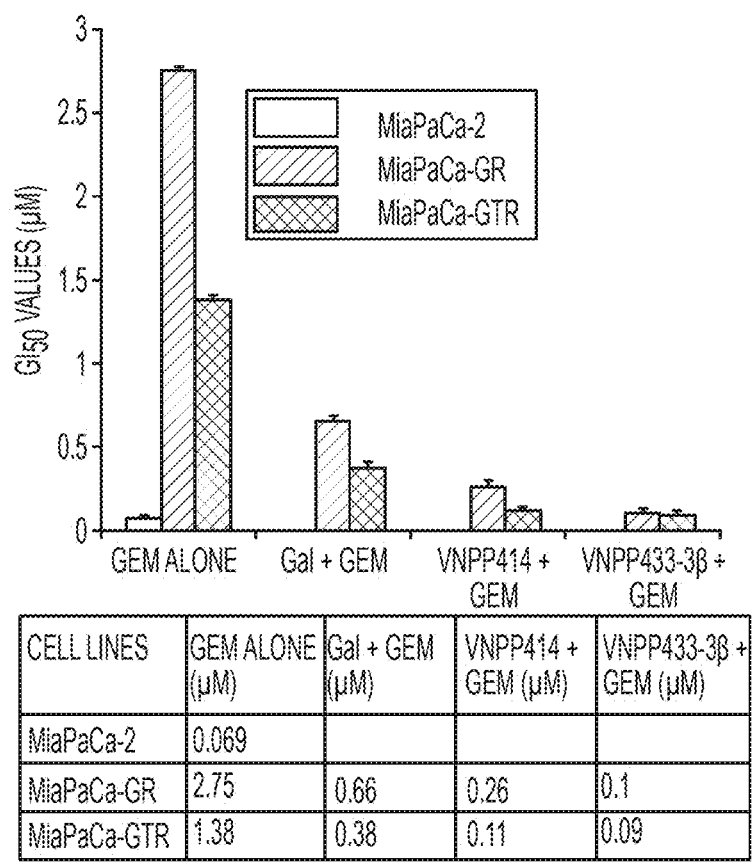
FIG. 8: Effect of Galeterone, analogs and Gemcitabine on PDAC cells. MTT assays were performed on Gem-resistant cells after sensitizing them with ARDAs and subsequently treated with gemcitabine.

Cell viability of ARDAs in PDAC cells were analyzed by MTT assay. MTT assays were performed on Gem-resistant cells after sensitizing them with ARDAs and subsequently treated with gemcitabine. As shown in FIG. 8, the addition of ARDAs to Gem inhibited the growth of MiaPaCa-GR and MiaPaCa-GTR Gem resistant cell lines in the mid nM to low M range. Galeterone and Gem in combination resulted in $GI_{50}$ values of 0.66 and 0.3 µM against MiaPaCa-GR and MiaPaCa-GTR, respectively. VNPP414 and Gem in combination resulted in $GI_{50}$ values of 0.26 and 0.11 µM against MiaPaCa-GR and MiaPaCa-GTR, respectively. VNPP433-313 and Gem in combination resulted in $GI_{50}$ values of 0.1 and 0.09 µM against MiaPaCa-GR and MiaPaCa-GTR, respectively.

Figure 9:
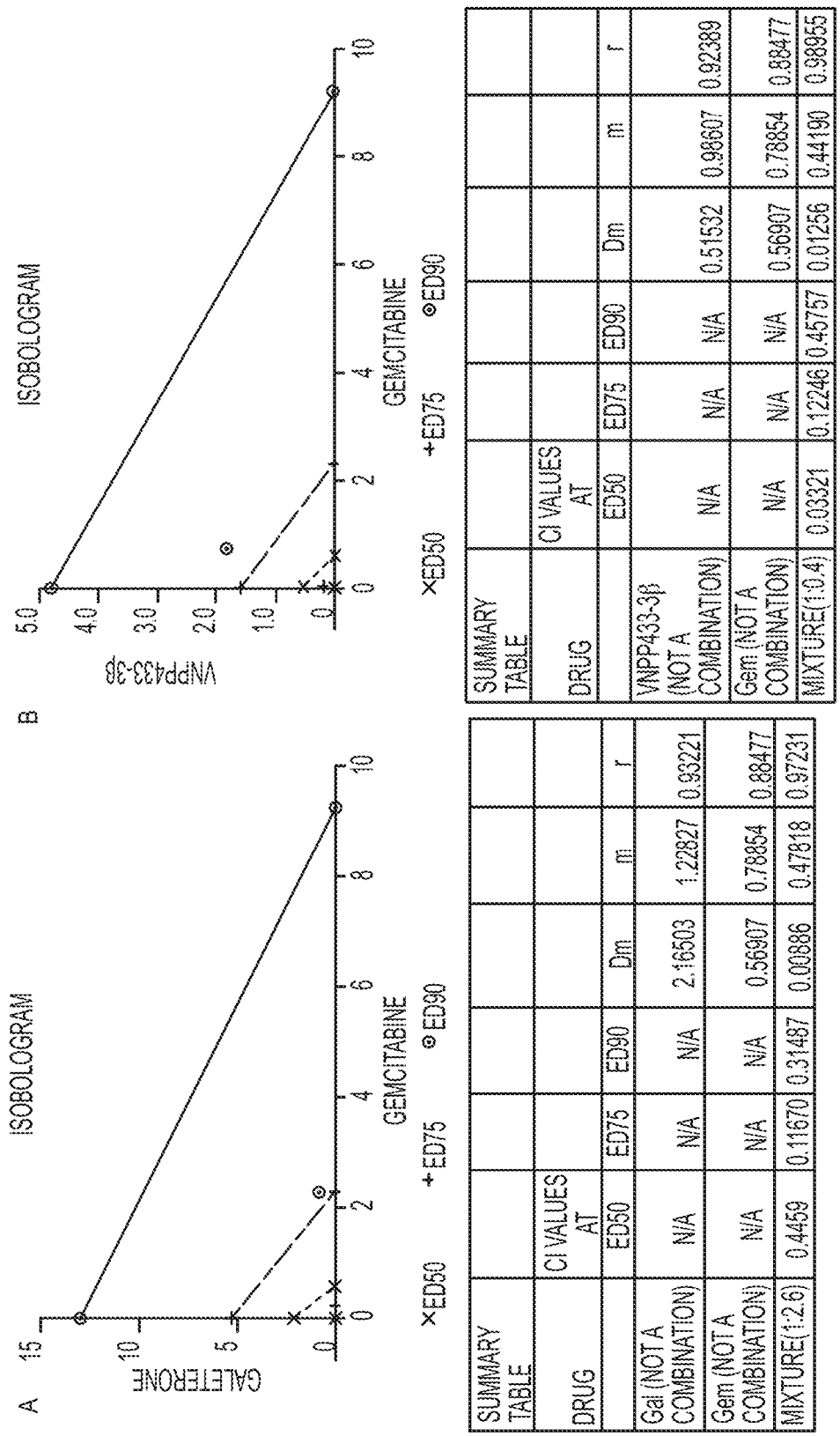
FIG. 9: Effect of Gal and Analogs in combination with Gemcitabine on Gem-resistant PDAC cells.

The antiproliferative activities of agents in the PDAC cell lines was also assessed. The strengths of combination, combination index (CI), was calculated using the Chou-Talalay method with CalcuSyn (Biosoft software) (where CI<1, synergy; CI=1, additivity; and CI>1, antagonism) (45). Isobolograms and combination index (CI) values were analyzed with the calcusyn software. Because this model requires fixed-dose ratios of test agents, cells are first treated with single agents in a dose response matrix to evaluate combination effects. Galeterone and VNPP433-313 were combined with Gemcitabine at their respective $GI_{50}$ values and the CI values determined using calcusyn (CI<1-synergy, CI=1-additive and CI>1-antagonism (FIG. 9A and FIG. 9B). Galeterone and VNPP433-313 sensitize gem-resistant cells and in combination with gemcitabine synergistically inhibits gem-resistant cells with CI values of 0.03-0.4. Combination studies could also reveal the activities of ARDAs as single agents versus this panel of PDAC cell lines. Finally, because the combination of EGF receptor (EGFR) inhibitor, erlotinib, with Gem has been the only drug tested so far to be superior to Gem alone (49), studies may also be done to compare combination data disclosed here with those of erlotinib and Gem.

Example 5: Activity of ARDAs and Gemcitabine Alone and in Combination on Colony Formation and Proteolytic Activity of MMP9

Figure 10:
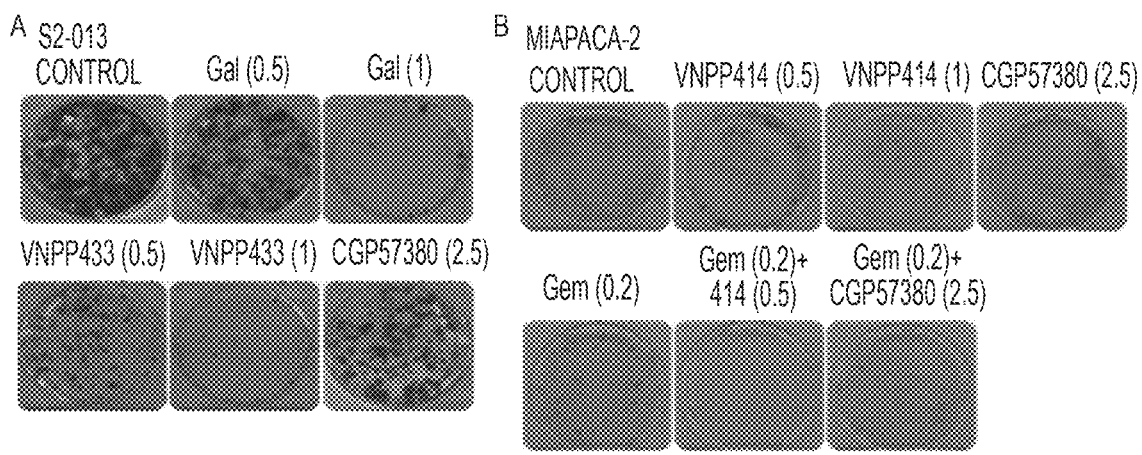
FIG. 10: Galeterone, analogs and Gemcitabine inhibit colony formation of Gem-naïve and Gem-resistant PDAC cells. S2-013 (FIG. 10A), MiaPaCa-2 (FIG. 10B) and MiaPaCa-GTR (FIG. 10C) show cells seeded at 1000 cells/well and treated with compounds (µM) for 14 days. Media was replaced every 72 hours. Cells were stained with 0.05% crystal violet. Conditioned media from MiaPaCa-2 cells after being treated with indicated compounds was separated on a zymogram gel to analyze the proteolytic activity of MMP9 after treatment (FIG. 10D).
Figure 10:
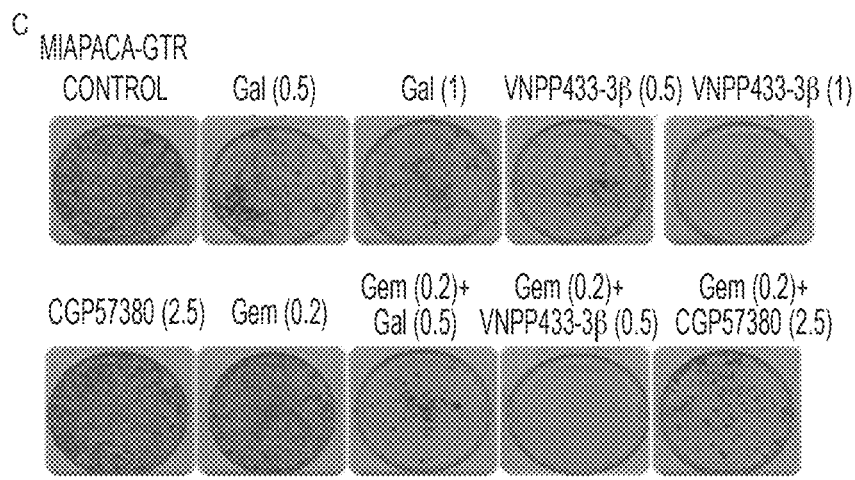
Figure 10:
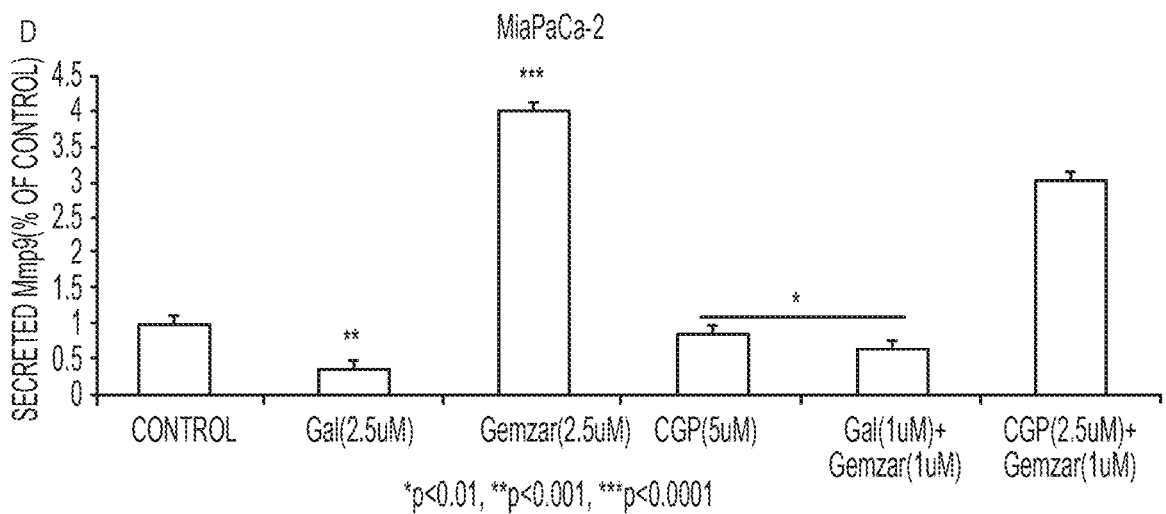
Figure 11:
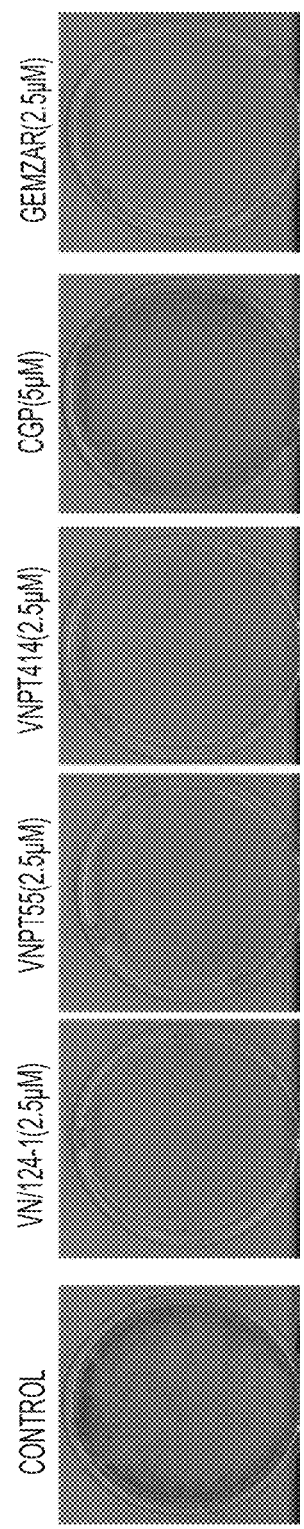
FIG. 11: Inhibition of colony formation in S2-013 cells.

The present Example shows the activity of ARDAs and Gemcitabine alone and in combination on colony formation and proteolytic activity of MMP9. Galeterone, analogs and Gemcitabine inhibit colony formation of Gem-naïve and Gem-resistant PDAC cells. S2-013, MiaPaCa-2 and MiaPaCa-GTR were seeded at 1000 cells/well and treated with compounds (µM) for 14 days. Media was replaced every 72 h. Cells were stained with 0.05% crystal violet (FIG. 10A-C). A similar experiment was performed in S2-013 cells and treatment with ARDAs resulted in inhibition of colony formation (FIG. 11). The results show that, whereas CGP (2.5 µM) did not significantly affect colony formation, ARDAs at 0. µM, significantly inhibited colony formation. Notably, the combination treatment (Gal or 414+Gem) almost completely suppressed colony formation (FIG. 10C), confirming a synergic effect. Colony formation, characteristics of metastatic cells to repopulate from a single cell, was significantly inhibited by galeterone and analogs either alone or in combination with gemcitabine in gem-naïve and gem-resistant cells.

Zymography assays were performed by seeding cells in 10 cm plates in phenol-red free media with no fetal bovine serum (FBS) and treated for 3 days. Media from cells were concentrated using amicon ultra filtration columns and normalized protein run on a 10% gelatin gels. Conditioned media from MiaPaCa-2 cells after being treated with indicated compounds was separated on a zymogram gel to analyze the proteolytic activity of MMP9 after treatment (FIG. 10D). Galeterone alone and or in combination with gemcitabine decreases MMP9 secretion. The ARDAs caused significant depletion of matrix metalloproteinases (MMPs).

Example 6: Further Characterization of the Activity of ARDAs and Gem Alone and in Combination The present Example describes studies that can be done to assess if apoptosis contributes to the anti-proliferative effects of ARDAs. Flow cytometry analysis can be performed for apoptosis and cell cycle distribution. The pan-caspase inhibitor, ZVAD-FMK and necrosis inhibitor, necrostatin-1 can be used to distinguish apoptosis from necrosis. To confirm proapototic effects, the extent to which gene silencing of Bax/Bad abrogates the activities can be analyzed. To determine the optimal sequence of agent administration, PDAC cells can be treated with ARDAs and Gemcitabine concurrently or sequentially at different time intervals. To minimize the difference in treatment duration between different agent-administration schedules, long-term cell survival using colony formation assays will can also be assessed. Another reported mechanism of drug-induced resistance in PDAC cells is through activation of autophagy (50-52). It can also be determined whether ARDAs reduce autophagy by causing caspase induced beclin1 cleavage to reduce autophagy and enhance apoptosis, using reported procedures (46, 47). Anti-androgens have recently been reported to induce autophagy in prostate cancer cells (53).

Example 7: ARDAs Inhibit Migratory and Invasive Potential of PDAC Cells

Figure 12:
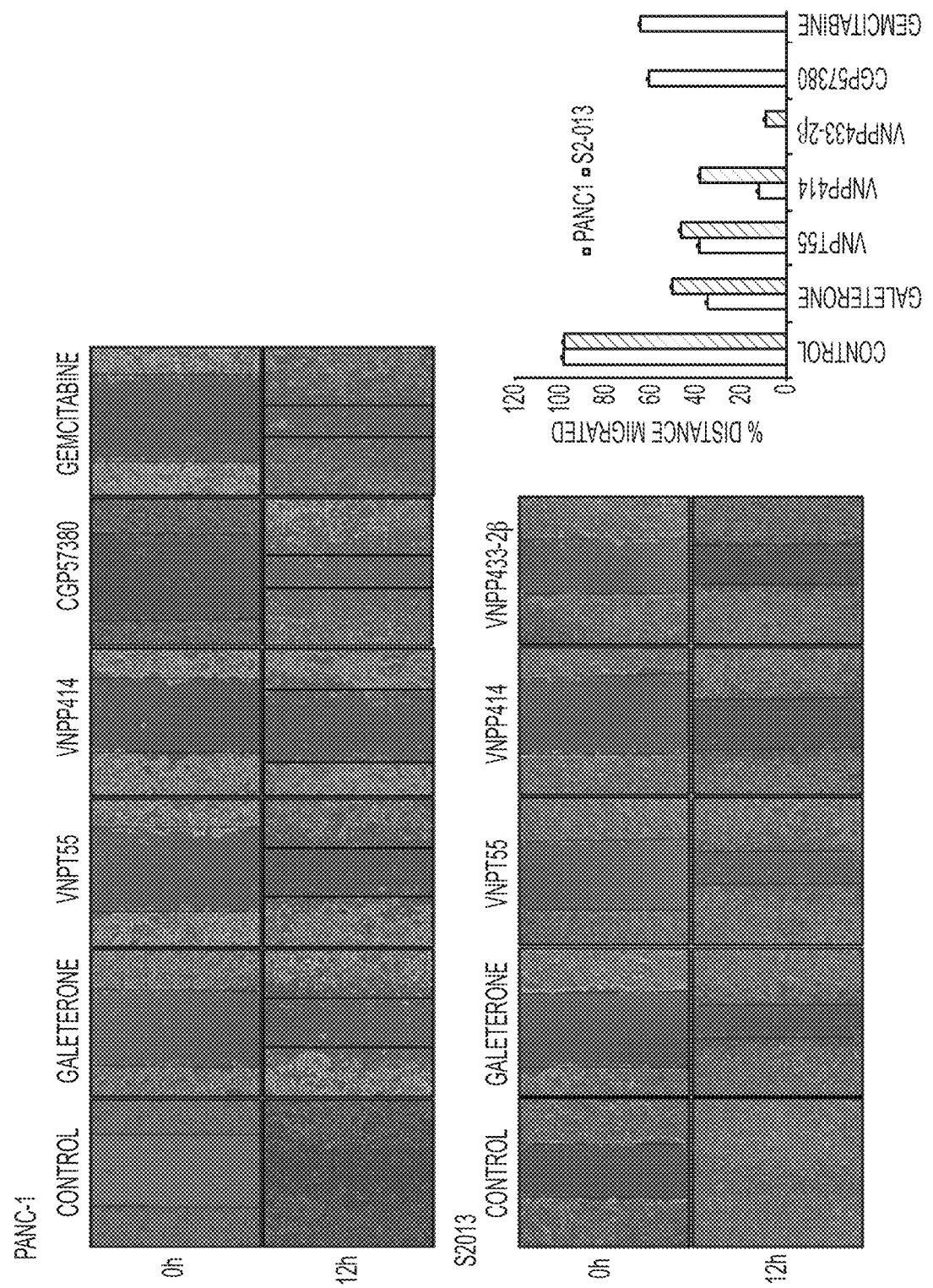
FIG. 12: Panc-1 and S2-013 cells plated in 24-well plate in a monolayer and scratch wound made with a 200 µl pipette tip and treated with indicated compounds at 5 µM for 12 hours.

The present Example investigates whether ARDAs inhibit the migratory and invasive potential of PDAC cells. Decreased invasive potential of PDAC cells was shown through wound-healing and matrigel-coated Boyden chambers assays. Cells grown to a monolayer were used in migration assay after a scratch was made and incubated for 12 hours. As shown in FIG. 12, wound-healing assays clearly demonstrate that in PANC-1 control cells, 12 h after cell monolayers were wounded; cells completely filled the cleared area. Gratifyingly, treatment Gal or VNPP414 caused significant inhibition of Panc-1 cells migration. In contrast, CGP and Gem were not effective. As expected these compounds also exerted strong anti-invasive efficacy against Capan-1 cells. The tested concentrations at time (12 h) of assay, all cells in each treatment group were ≥90% viable.

Figure 13:
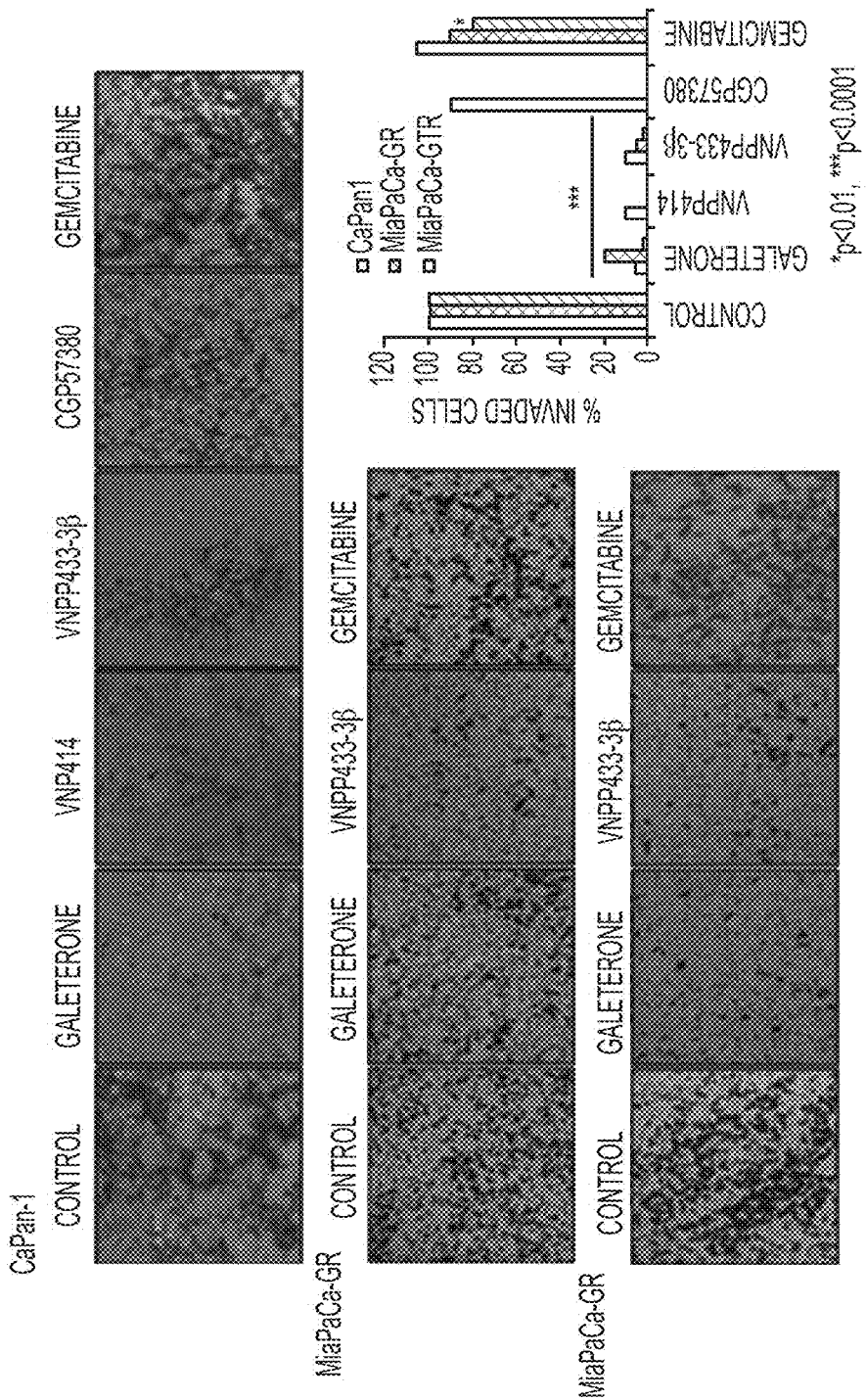
FIG. 13: Anti-migratory and anti-invasive activities of Galeterone, analogs and Gemcitabine on Gem-naïve and Gem-resistant PDAC cells. CaPan-1 and gem-resistant (MiaPaCa-GR) and gem/erlotinib-resistant cells (MiaPaCa-GTR) were plated in matrigel coated Boyden chambers treated with indicated compounds at 5 µM for 24 hours with chemo attractant in the bottom chamber.

Invasion assays were carried out in matrigel coated Boyden chambers. CaPan-1 and gem-resistant (MiaPaCa-GR) and gem/erlotinib-resistant cells (MiaPaCa-GTR) were plated in matrigel coated Boyden chambers treated with indicated compounds at 5 µM for 24 h with chemo attractant in the bottom chamber (FIG. 13).

Example 8: ARDAs Deplete Cdc25 Protein and Cause Cell Cycle Arrest

Figure 17:
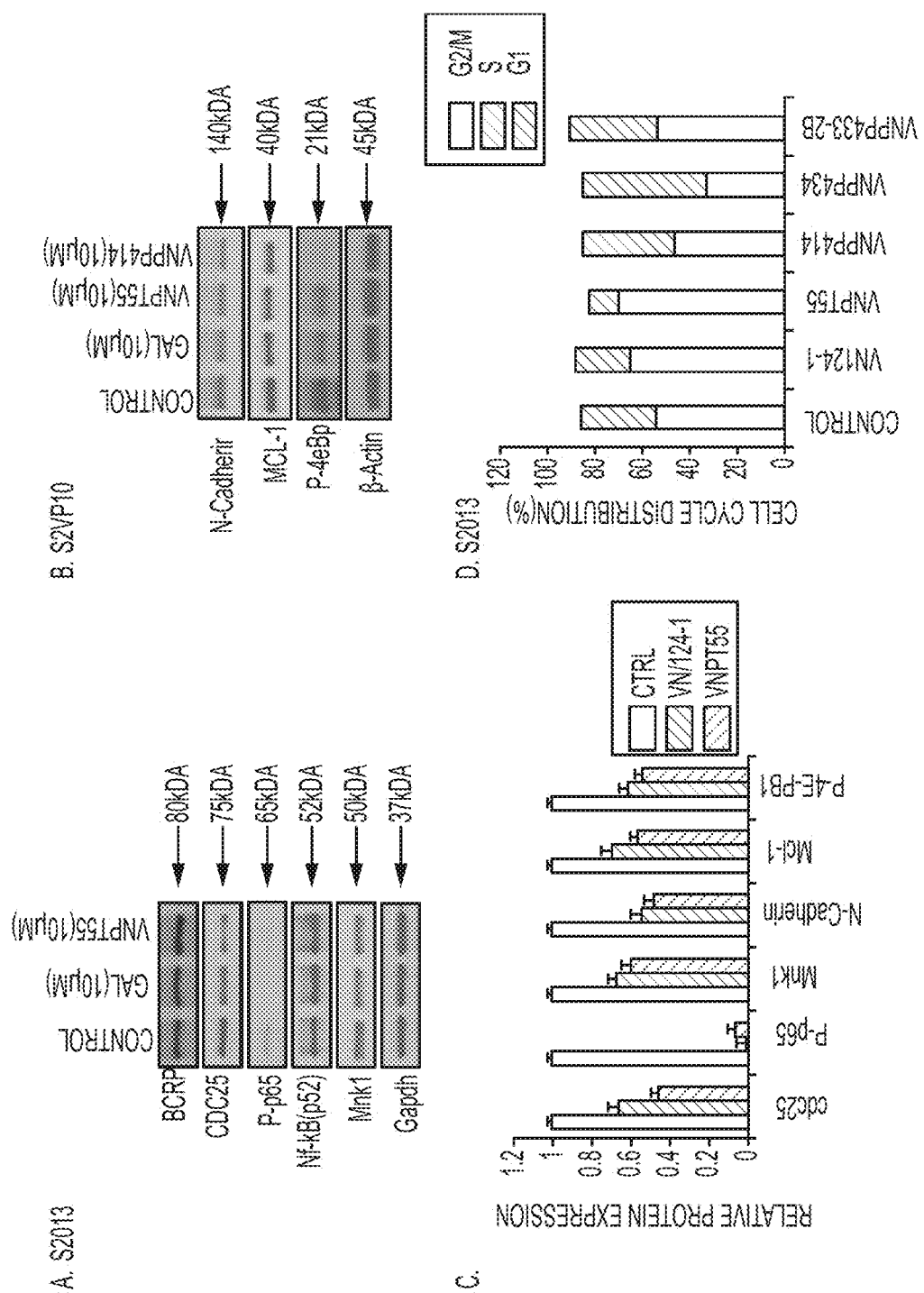
FIG. 17: ARDAs deplete cdc25 protein and cause S-phase cell cycle arrest.

The present Example shows the effect on cell cycle contributed by the anti-proliferative effects of ARDA compounds. Flow cytometry analysis for cell cycle distribution was performed. Protein expression was analyzed by western blot and densitometry quantified with Imagej. ARDAs deplete cdc25 protein and cause S-phase cell cycle arrest in S2-013 pancreatic cancer cells (FIG. 17). Effects on cell cycle proteins (cdc25c, cyclins) may be the cause of cell cycle arrest post treatment with ARDAs. Analysis of the western blot data in (FIG. 17A) also shows that although 50% of pancreatic cancers lose the 4E-BP1, this phosphorylation is also inhibited, with significant depletion of Nf-κB phosphorylation. Analysis by western blot in S2VP10 cells is also shown in FIG. 17B.

Figure 14:
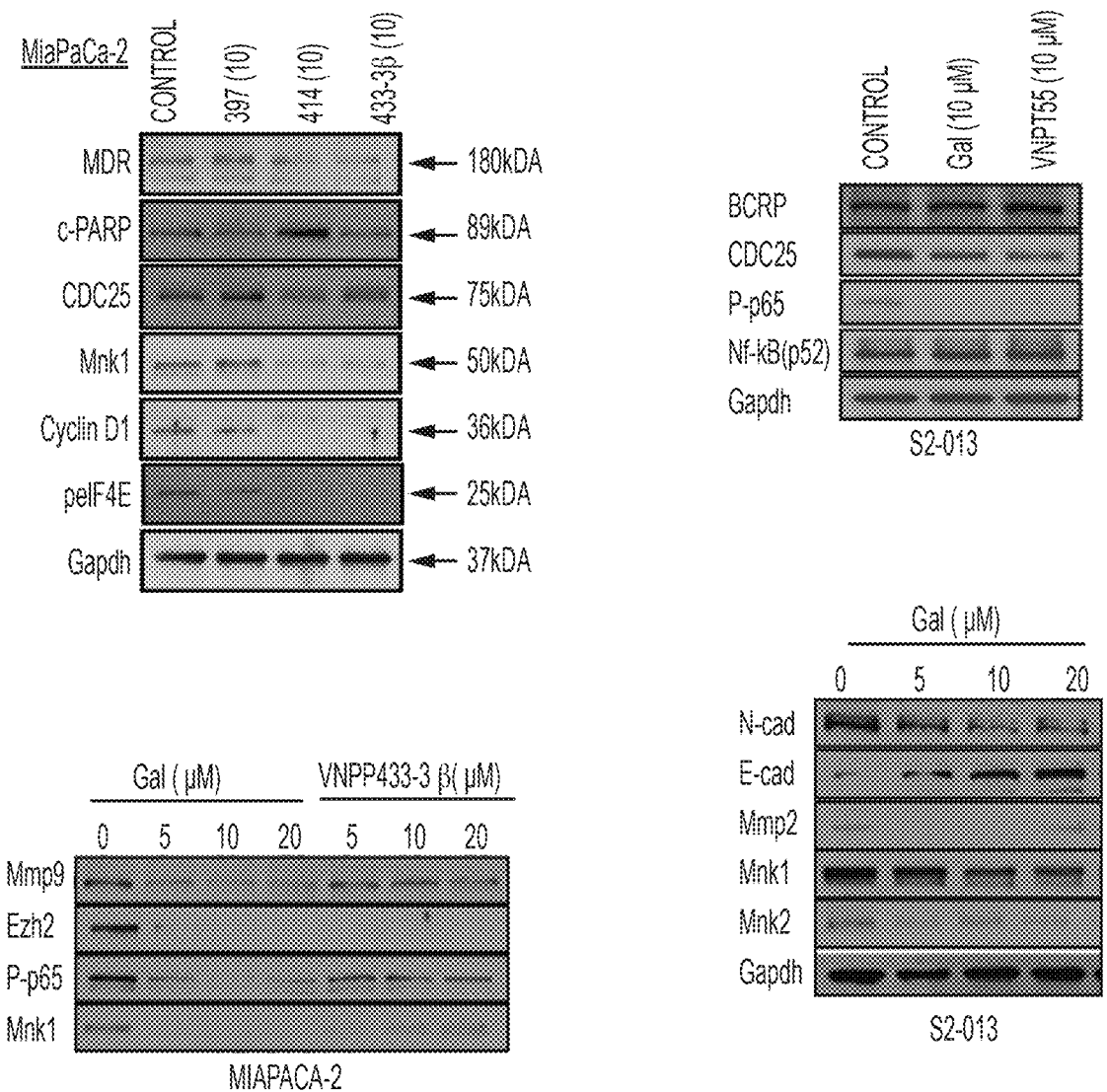
FIG. 14: Effects of Gal and analogs on significant onco-targets. MiaPaCa-2 and S2-013 cells were used to investigate key resistant proteins and factors involved in EMT. Numbers in prentices are concentration in µM.
Figure 15:
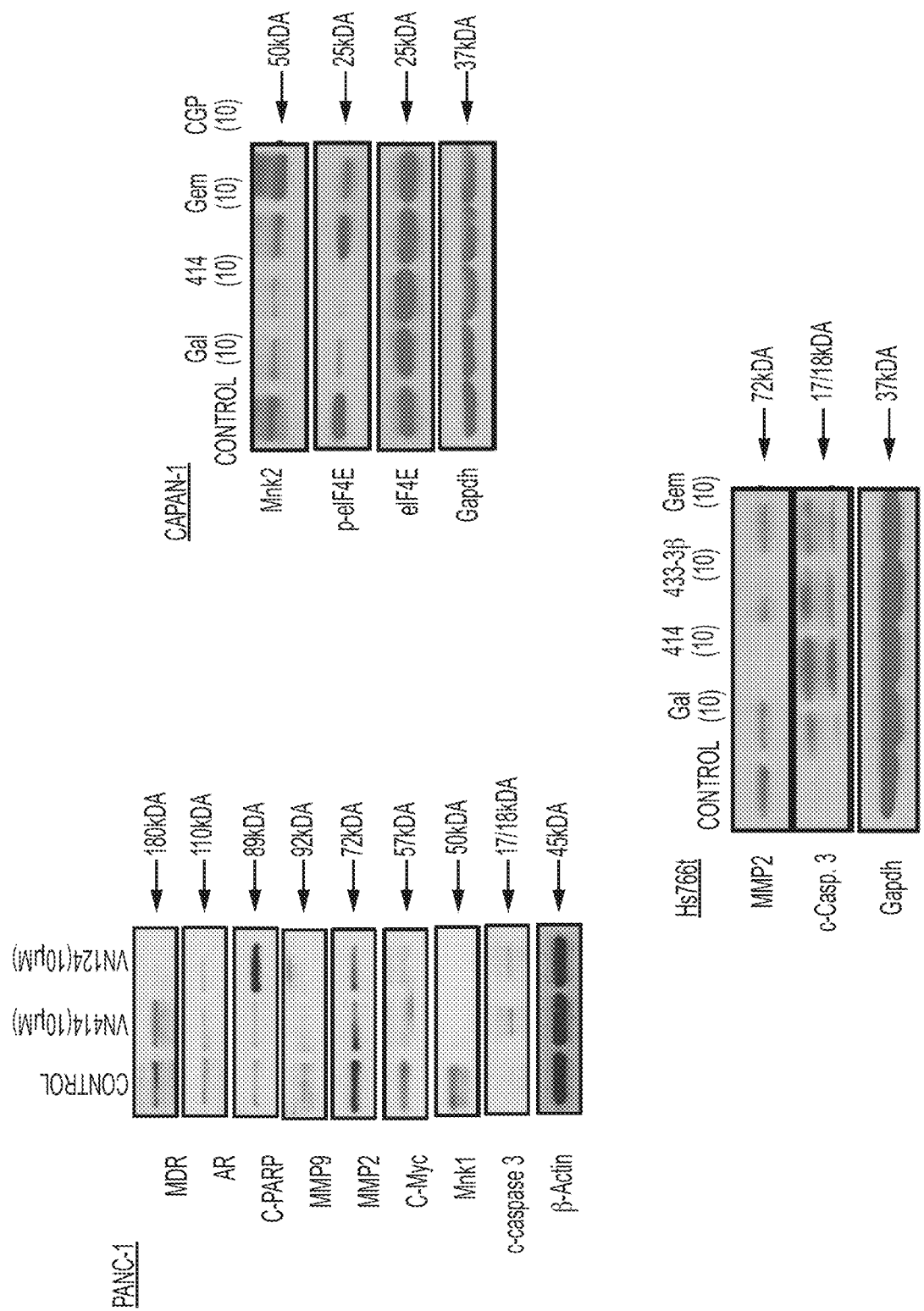
FIG. 15: Effects of Gal and analogs on significant onco-targets. Panc-1, HS776T and CaPan1 cells were treated with 10 µM of indicated compounds for 24 hours and protein expression analyzed. Numbers in prentices are concentration in µM.
Figure 18:
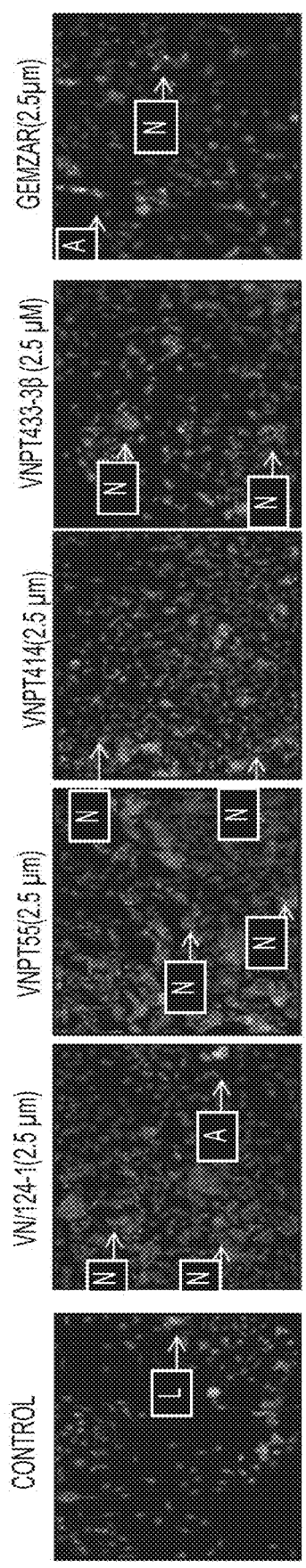
FIG. 18: Apoptotic induction of Gal and Analogs and Gem-resistant PDAC cells.
Figure 18:
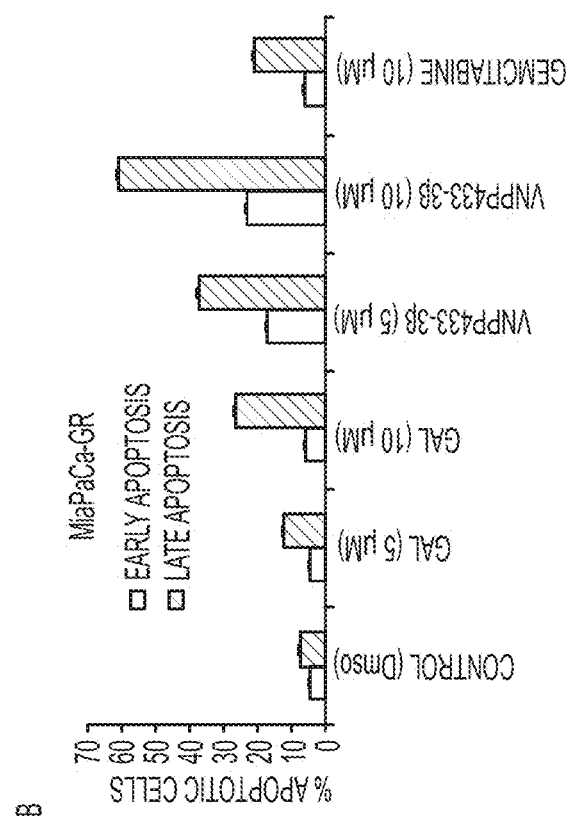

Example 9: ARDAs Induce Apoptosis and Inhibit Migration of Pancreatic Cancer Cells The present Example shows ARDAs effect on inducing apoptosis. Immunoblot analysis of treated lysates revealed induction of apoptosis via caspase 3 cleavage (FIG. 15). Cells treated with indicated doses for 24 hours were analyzed by acridine orange ethidium bromide assay and also by FACS analysis using Annexin V and PI staining following manufacturer's protocol. Galeterone and analogs significantly induce apoptosis in metastatic cell line (S2-013) and in MIaPaCa-GR cells (FIG. 18). Galeterone and analogs induce apoptosis in S2-013 cells analyzed by acridine orange ethidium bromide staining (FIG. 14A). Galeterone and analogs were compared to gemcitabine in inducing both early and late apoptosis analyzed by flow cytometry (FIG. 18B). Flow cytometric analysis showed that ARDAs significantly induced apoptosis in gem-resistant PDAC.

Example 10: ARDAs Effectively Modulate Oncogenic Proteins

The present Example shows the effects of ARDAs, including Galeterone, on several oncogenic proteins in PDAC cell lines. Western blot was used to examine the effects of agents/drug (single-agent versus combination) on the levels of Mnk1/2 and peIF4E (active form of eIF4E), because of their well-established implication in PDAC initiation, progression metastasis and drug resistance (2, 5, 19).

PDAC cells were treated with compounds at indicated concentrations, followed by Western blotting analyses. MiaPaCa-2 and S2-013 cells were used to investigate key resistant proteins and factors involved in EMT (FIG. 14). As shown in FIGS. 14 and 15, the agents caused marked depletion of Mnk1/2, peIF4E and AR, with concomitant selective repression of potent growth and survival factors (cyclin D1, CDC25, c-myc, MMP2, MDR, NF-κB/p-p65), and caused up-regulation of apoptotic markers (c-caspase 3 and c-PARP). Resistance inducing proteins such as MDR are downregulated by ARDAs in both AR positive and negative pancreatic cancer cells. Mnk1 depletion also affects c-Myc, cyclin D1, MMP9 and MMP2 expression. EZH2, a prominent metastatic enhancing gene in pancreatic cancer was also downregulated at the protein level. Western blot analysis show inhibitory effects on the translational machinery (Mnk1/2-eIF4E axis) and also on resistant inducing protein NF-κB(p65) phosphorylation.

Figure 16:
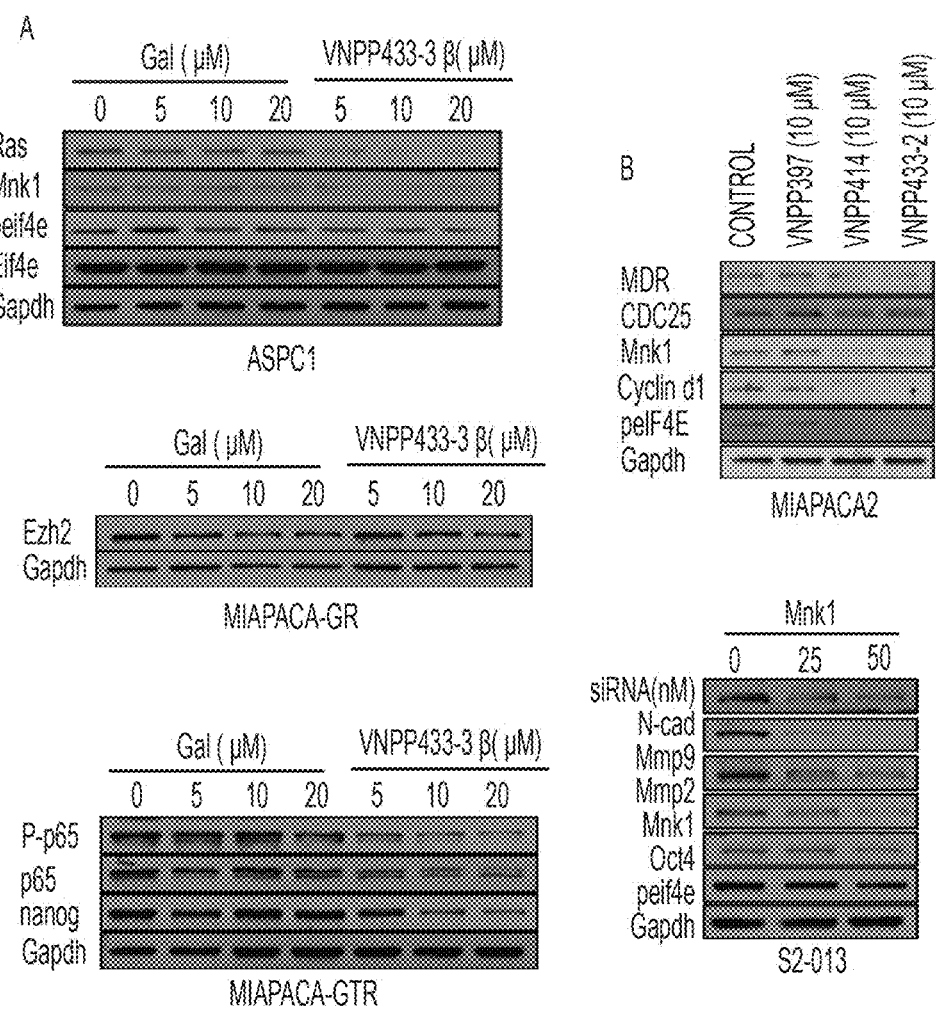
FIG. 16: Effects of Gal and analogs on significant onco-targets.

Gene silencing approaches can be used to determine the extent to which silencing of Mnk1 or Mnk2 plus ARDAs or ARDAs+Gem phenocopies the single agent and drug combination cell viability, cell cycle analysis, Annexin V apoptosis analysis and Western blot. ASPC1 and gem-resistant cells were analysed to investigate the effects on EZH2, Ras, p65 and nanog (FIG. 16A). Knockdown of Mnk1 with siRNA shows downstream effects on MMP-2/9 and peIF4E (FIG. 16B).

Example 11: Define the Role of NF-κB in the Actions of ARDAs as Single Agents and in Combination The present Example describes experiments that can be done to define the role of NF-κB in the actions of ARDAs as single agents and in combination. Because PI3K-Akt-mTOR activation in pancreatic cancer is also known to activate the NF-κB pathway (55) implicated in PDAC progression, resistance and metastasis and because ARDAs potently down-regulate mTOR, and NF-κB (p65) phosphorylation, the role of NFκ-B in the actions of ARDAs and their combinations with Gem may be important. If inhibition of NFκ-B is discovered to be critical for potent anti-proliferative activities and/or strong synergy with Gem, NF-κB inhibitors can be employed (such as parthenolide) to further confirm its significance in the single-agent and combination actions (56). Because ARDAs markedly modulate downstream targets of NF-κB such as Cox-2, MMP-3/9, Bcl-2, c-Myc, and cyclin D1, the depletion of NF-κB may play key role in the efficacy of ARDAs and combination with Gem against PDAC cell lines.

Example 12: Other Mechanisms of Action

The present Example describes other potential mechanisms of action of ARDAs. ARDAs inactivate resistance-inducing pathways and sensitize PDAC cells to Gem. Other potential pathways that could possibly play a role in the mechanism of action of ARDAs are the reactivation of tumor suppressor genes (ERβ and RARβ) and specific targeting of genes such as RKIP (Raf kinase inhibitor protein) at protein level and/or transcription level. Furthermore, other mechanisms of PDAC resistance could be involved, including multidrug resistance proteins (MDR) and other efflux pumps (ABCG) (57), BCRP and solute carriers (hENT1 and hCNT3) (58). The role of androgen receptor (AR) on the action of our ARDAs in PDAC proliferation, resistance and metastasis can also be investigated.

Example 13: Determining Anti-Tumor and Anti-Metastatic Efficacies of ARDAs Versus Gemcitabine in Animal Models of PDAC The present Example describes studies that can be done to evaluate antitumor efficacy of ARDAs versus gemcitabine, for example, in three potentially clinically relevant in vivo models: MiaPaCa-2 xenograft model, MiaPaCa-2-luc orthotopic model and a KRAS driven patient derived xenograft (PDX) PDAC model. This Example also describes studies that can identify biomarkers of efficacy that may be useful in future clinical trials.

By utilizing complementary PDAC cell lines and three in vivo models, including a patient-derived xenograft model, successful completion of the proposed studies, are expected to identify key molecular determinant for the sensitivity of these disclosed ARDAs. Furthermore, this will establish their strong anti-tumor activities, either alone (single agents) or in combination with gemcitabine in PDAC cells in vitro. The in vivo studies will establish our ARDAs's anti-tumor and anti-metastasis efficacies in clinically relevant models of PDAC. Thus, data obtained from the proposed study will provide strong preclinical proof-of-concept for the use of multi-target ARDAs as a therapeutic strategy in the treatment of pancreatic cancer.

Example 14: Evaluation of Therapeutic Efficacy of ARDAs in Models of Human Pancreatic Cancer The present Example describes studies that can be done to evaluate the therapeutic efficacy of ARDAs in models of human pancreatic cancer. On the basis of data disclosed here, which shows that ARDAs (VN/124-1, VNPP414, and VNPP433-3β) possess potent anti-tumor activities and anti-metastatic potentials, relevant PDAC models can be used, including, xenograft of AsPc-1 tumors MiaPaCa-2 tumors, orthotopic model of MiaPaCa-2-luc tumors and patient-derived xenograft (PDX) model. MaiPaCa-2 tumor models can be chosen for this study because of their relatively resistant nature (30, 59). A PDX model harboring KRAS mutations with gene amplification could also be used. This is based on the findings that human pancreatic cancer cell lines with KRAS gene amplifications have been shown to exhibit greater degrees of KRAS dependency (60). In addition, PDX tumors, unlike xenograft tumors established from pancreatic cancer cell lines, preserve key features of PDAC, such as invasiveness, desmoplastic reaction, tumor vasculature and cellular diversity (60, 61).

Combination studies of a lead ARDA with gemcitabine or erlotinib in animal models of PDAC can also be performed. Combination studies of ARDA compounds with therapies such as those listed in Example 19 may also be performed. Gemcitabine can be used as a positive control in the xenograft and orthotopic models studies; and dose selection will be guided by experience with the doses of VN/124-1 (Gal) used in anti-tumor efficacy studies in xenograft models of prostate cancer (62-65).

Example 15: Anti-Tumor Efficacy Studies

The present Example describes how the antitumor efficacy of ARDAs in xenograft models can be evaluated. The xenograft model of MiaPaCa-2 tumors using procedures reported previous can be used (30, 59, 66, 67). Anti-tumor efficacy evaluation using the patient-derived xenograft PDX model can mimic the potential effects of ARDAs in humans. These studies will test the efficacy of at least two compounds (to be determined by results of their efficacies in the subcutaneous and orthotopic models).

Example 16: Anti-Metastasis Efficacy Studies

The present Example describes studies that can be used to determine the anti-metastatic potential of ARDA compounds using orthotopic PDAC MiaPaCa-2-luc cells (transfected with luciferase) implanted into the pancreas following a well-established literature procedure (68, 69). The effects of ARDAs on metastasis can be assessed at the end of the study via pathological analysis of tumors and other body organs. Thus, tumors will be excised and embedded for histologic analysis of tumor growth, invasion, and metastasis (pancreatic tumor, pancreas, liver, lymph nodes and lungs). Additionally, this model can also be used to provide another technique (using non-invasive IVIS bioluminescence imaging system) to evaluate the antitumor efficacy of our ARDAs. Biomarkers of ARDAs efficacies determined by above Examples can also be assessed in tumors.

Example 17: Potential Toxicity

The present Example describes potential solutions regarding toxicity of the ARDA compounds. All three ARDAs disclosed here may be effective in resulting in regression and/or suppression of PDAC tumors and inhibition of metastasis. Unexpected toxicity may be encountered in these in vivo studies. This problem can be addressed by lowering the doses and/or administration frequency of the test compounds.

Example 18: Advanced Preclinical Studies

The present Example describes studies that can be used to determine the effect of ARDAs in preclinical models of pancreatic cancer. The near-term impacts of the present invention can be the development of simple and high-yield methods for the production of lead ARDAs (VN/124-1, VNPP414 and VNPP433-3β), and preliminary validation of therapeutics for an urgent, unmet need in pancreatic cancer treatment. The ARDAs may effectively suppress Mnk-eIF4E in preclinical models of pancreatic cancer and effectively slow or reverse tumor growth and metastasis. In addition, these agents can be effective against drug-resistant PDAC cells and enhance drug (gemcitabine) chemosensitivity and reverse resistance. Rigorous advanced preclinical testing can also be performed, including robust formulation, pharmacokinetics, toxicity and pharmacodynamics studies. An effective modulator of oncogenic protein translation could radically improve successful treatment of difficult-to-treat pancreatic cancer, as well as other Mnk/eIF4E-driven tumors, such as other solid tumors (prostate, breast, colon, lungs, liver, gliomas, etc.) and hematologic diseases.

Example 19: Drugs Approved for Pancreatic Cancer

The present Example lists drugs that are currently approved for treatment of pancreatic cancer. Currently the following compounds are approved for use in treating patients with pancreatic cancer: Abraxane (Paclitaxel Albumin-stabilized Nanoparticle Formulation), Adrucil (Fluorouracil), Afinitor (Everolimus), Efudex (Fluorouracil), Erlotinib Hydrochloride, Everolimus, Fluoroplex (Fluorouracil), Fluorouracil, Gemcitabine Hydrochloride, Gemzar (Gemcitabine Hydrochloride), Mitomycin C, Mitozytrex (Mitomycin C), Mutamycin (Mitomycin C), Paclitaxel Albumin-stabilized Nanoparticle Formulation, Sunitinib Malate, Sutent (Sunitinib Malate) and Tarceva (Erlotinib Hydrochloride). Drug combinations such as FOLFIRINOX, GEMCITABINE-CISPLATIN. GEMCITABINE-OXALIPLATIN and OFF have also been approved as combination treatments for pancreatic cancer. Lanreotide Acetate and Somatuline Depot (Lanreotide Acetate) are available for of grastroenteropancreatic neuroendocrine tumors.

Example 20: Exemplary Synthesis of Compounds

The Examples describe synthetic routes to ARDA compounds, VNPP414 and VNPP433-3β.

Example 20.1. Lead Optimization of VN 124-1 (Galeterone)

Compounds were developed with enhanced androgen receptor downregulating and/or degrading (ARD) activities compared to our clinical candidate VN/124-1 (TOK-001 or galeterone), that will soon enter Phase III clinical studies in which it will be administered to castration resistant prostate cancer (CRPC) patients. For example, the corresponding 3β-carbamate (VNPT-55) (Scheme 1) was developed. Compared to VN/124-1, VNPT-55 is 4- and 8-fold more potent with respect to anti-proliferative (AP) and ARD activities, respectively (1). Concerns of potential in vivo instability of VNPT-55 led to the design and synthesis of VNPP414 and VNPP433-313 (Scheme 1), albeit in very low yields, of 12 and 11%, respectively. Because of their promising anti-cancer activities, a more expeditious and practical syntheses of VNPP414 and VNPP433-313 is included in the present invention.

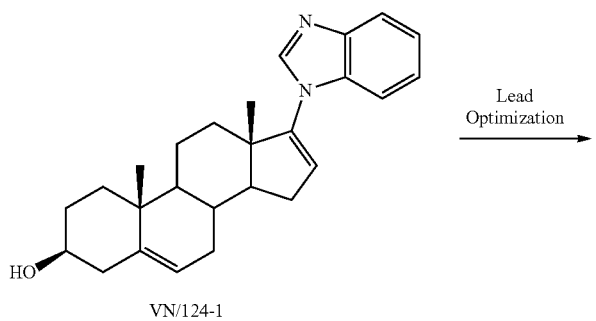

VN/124-1

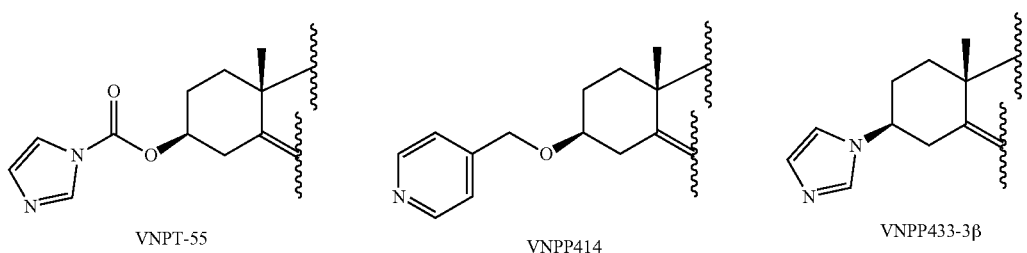

VNPT-55  VNPP414  VNPP433-3β

Example 20.2. Practical Synthesis of VNPP414

Early attempts to synthesize VNPP414 utilized the Williamson's ether synthesis method where VN/124-1 was treated with the commercially available 4-(bromomethyl)pyridine hydrobromide with NaH/DMF to afford VNPP414 in low (12%) yield (1). However, based on observations that the use of 3-(iodomethyl)pyridine hydrochloride under identical conditions produced the corresponding 3-pyridyl ether of VN/124-1 in good yield (56%) (1), the latter procedure can be adapted for practical synthesis of VNPP414. Iodoaryl/alkyl halides yield superior yield of the desired ether. Thus, the commercially unavailable 4-(iodomethyl)pyridine hydrochloride (2) is synthesized from readily available 4-pyridine carbinol (1) (32), followed by etherification with VN/124-1 as shown in Scheme 2. Several alternative procedures that can be readily utilized: (i) the useful variation of the Williamson synthesis which involves the use of silver oxide, Ag$_2$O, as base rather than NaH (33); (ii) by adopting the reported Dudlay's mild and neutral conditions of alcohol benzylation, using 2-(4-pyridyl)methoxyloxy-1-methyl pyridinium triflate (34) and treatment with VN/124-1 in the presence of MgO (35) (Scheme 3A); and (iii) use of Mitsunobu etherification procedure following treatment of VN/124-1-3α-mesylate with commercially available 4-pyridine carbinol (36) (Scheme 3B).

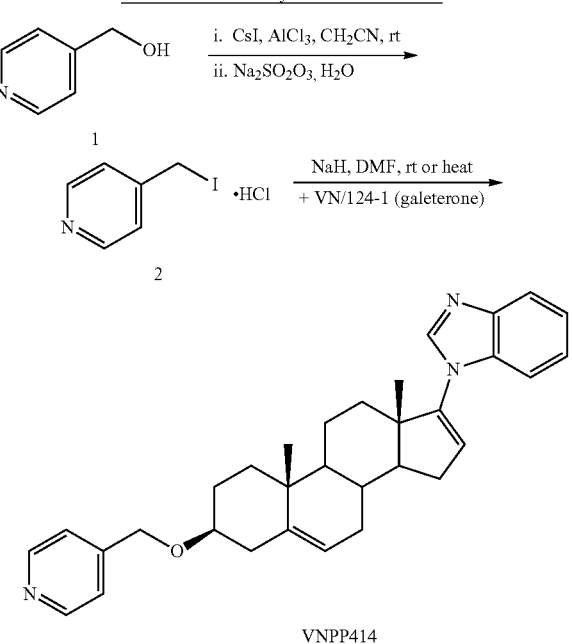

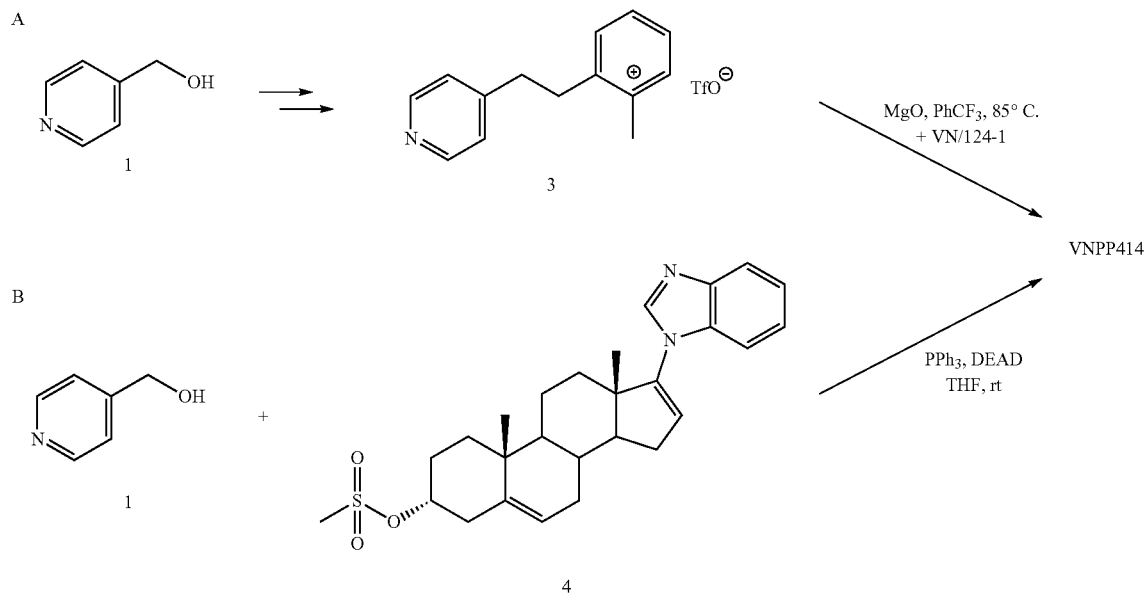

Example 20.3. Practical Synthesis of VNPP433-3β

The initial attempt to obtain VNPP433-3β by reaction of VN/12-4-3β-mesylate with imidazole resulted in a mixture of three steroidal imidazoles and other products, including VNPP4333β in only 11% yield. It was noted that because of the well-established participation of the homoallylic double bond at the $C_5$ position of steroids similar to VN/124-3β-mesylate, the above substitution reaction suffered from poor stereoselectivity, elimination, and rearrangement (37). To overcome this limitation, procedures outline here were designed to circumvent possible participation of the steroidal $\Delta^5$ double bond. Thus, VNPP433-3β was synthesized as outlined in Scheme 4. VN/124-1 can be converted to the α-p-nitrobenzoic acid ester (5) via Mitsunobu method, using diethylcarboxylate (DEAD and $PPh_3$ (38). Hydrolysis of 5 followed by mesylation will afford compound 4. Treatment of 4 with $NaN_3$ and 15-crown-5 ether in DMF (39) will give the 3β-azide (6). Alternatively, compound 6 will be prepared using the method for stereoselective azidonation of 3β-mesylate of VN/124-1 using $TMSN_3$ in the presence of boron trifluoride etherate ($BF_3 \cdot OEt_2$) in DMC (37). The azide (6) will be reduced to 3β-amine (7) by reacting with $PPh_3$ in MeOH/THF (40) or by reduction with LiAlH4 in ether (37). Finally, cyclization of amine by treatment with glyoxal, formaldehyde and ammonia (41), will afford the desired imidazole, VNPP433-3β.

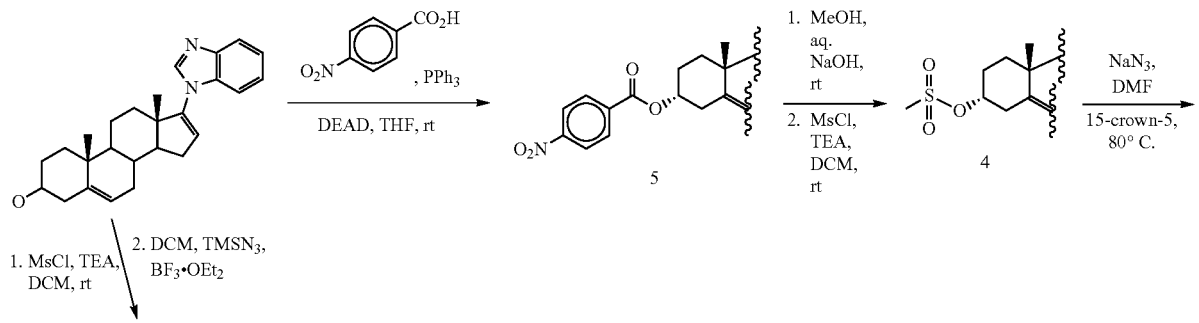

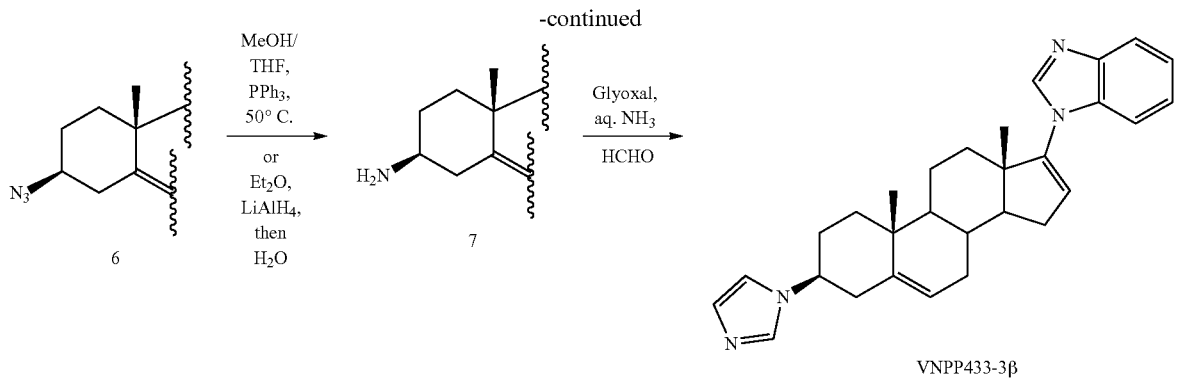

Alternative routes to VNPP433-3β, are outlined in Scheme 5A-C. In Scheme 5A, imidazole is condensed to 3-iododiene key intermediate (8), (42) followed by selective reduction using NaBH₄ to give VNPP433-3β. Schemes 5B & C utilized strategies that mask/protect Δ⁵ double bond prior to introduction of the 3-imidazole, involving reactions that have previously been used (1, 43, 44).

REFERENCES

1. Purushottamachar P, Godbole A M, Gediya L K, Martin M S, Vasaitis T S, Kwegyir-Afful A K, et al. Systematic structure modifications of multitarget prostate cancer drug candidate galeterone to produce novel androgen receptor down-regulating agents as an approach to treatment of

A

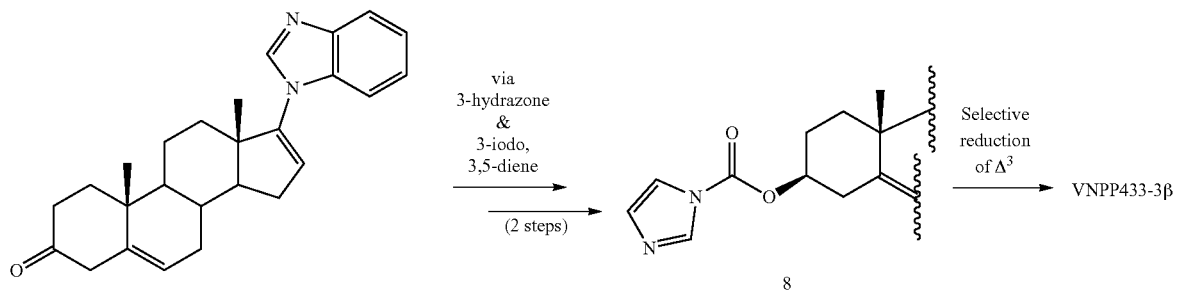

B & C

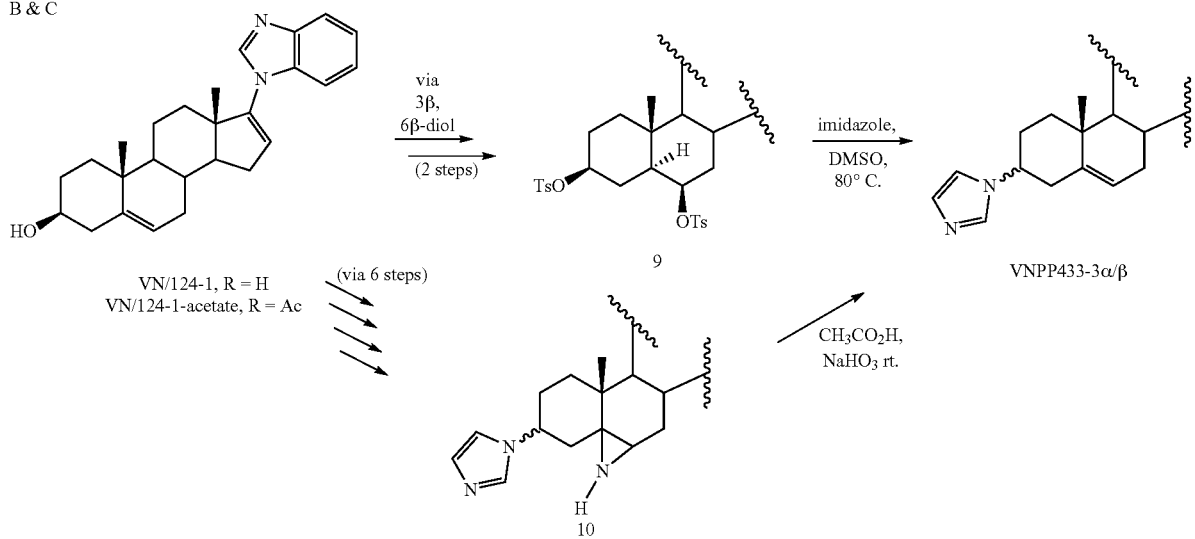

advanced prostate cancer. Journal of medicinal chemistry. 2013; 56(12):4880-98. Epub 2013/05/30.
2. Adesso L, Calabretta S, Barbagallo F, Capurso G, Pilozzi E, Geremia R, et al. Gemcitabine triggers a pro-survival response in pancreatic cancer cells through activation of the MNK2/eIF4E pathway. Oncogene. 2013; 32(23): 2848-57. Epub 2012/07/17.
3. Martineau Y, Azar R, Muller D, Lasfargues C, El Khawand S, Anesia R, et al. Pancreatic tumours escape from translational control through 4E-BP1 loss. Oncogene. 2013; 33:1367-74.
4. Okitsu K, Kanda T, Imazeki F, Yonemitsu Y, Ray R B, Chang C, et al. Involvement of interleukin-6 and androgen receptor signaling in pancreatic cancer. Genes & cancer. 2010; 1(8):859-67. Epub 2011/07/23.
5. Robichaud N, Del Rincon S V, Huor B, Alain T, Petruccelli L A, Hearnden J, et al. Phosphorylation of eIF4E promotes EMT and metastasis via translational control of SNAIL and MMP-3. Oncogene. 2014. Epub 2014/06/10.
6. Ottenhof N A, de Wilde R F, Maitra A, Hruban R H, Offerhaus G J. Molecular characteristics of pancreatic ductal adenocarcinoma. Pathology research international. 2011; 2011:620601. Epub 2011/04/23.
7. Siegel R, Ma J, Zou Z, Jemal A. Cancer statistics, 2014. CA: a cancer journal for clinicians. 2014; 64(1):9-29. Epub 2014/01/09.
8. Magee C J, Ghaneh P, Neoptolemos J P. Surgical and medical therapy for pancreatic carcinoma. Best practice & research Clinical gastroenterology. 2002; 16(3):435-55. Epub 2002/06/25.
9. di Magliano M P, Logsdon C D. Roles for KRAS in pancreatic tumor development and progression. Gastroenterology. 2013; 144(6):1220-9. Epub 2013/04/30.
10. Mendoza M C, Er E E, Blenis J. The Ras-ERK and PI3K-mTOR pathways: cross-talk and compensation. Trends in biochemical sciences. 2011; 36(6):320-8. Epub 2011/05/03.
11. Bitterman P B, Polunovsky V A. Attacking a nexus of the oncogenic circuitry by reversing aberrant eIF4F-mediated translation. Molecular cancer therapeutics. 2012; 11(5): 1051-61. Epub 2012/05/11.
12. Bitterman P B, Polunovsky V A. Translational control of cell fate: from integration of environmental signals to breaching anticancer defense. Cell Cycle. 2012; 11(6): 1097-107. Epub 2012/02/24.
13. Hay N. Mnk earmarks eIF4E for cancer therapy. Proceedings of the National Academy of Sciences of the United States of America. 2010; 107(32): 13975-6. Epub 2010/08/04.
14. Mamane Y, Petroulakis E, Rong L, Yoshida K, Ler L W, Sonenberg N. eIF4E—from translation to transformation. Oncogene. 2004; 23(18):3172-9. Epub 2004/04/20.
15. Topisirovic I, Ruiz-Gutierrez M, Borden K L. Phosphorylation of the eukaryotic translation initiation factor eIF4E contributes to its transformation and mRNA transport activities. Cancer research. 2004; 64(23):8639-42. Epub 2004/12/03.
16. Wendel H G, Silva R L, Malina A, Mills J R, Zhu H, Ueda T, et al. Dissecting eIF4E action in tumorigenesis. Genes & development. 2007; 21(24):3232-7. Epub 2007/12/07.
17. Konicek B W, Dumstorf C A, Graff J R. Targeting the eIF4F translation initiation complex for cancer therapy. Cell Cycle. 2008; 7(16):2466-71. Epub 2008/08/23.
18. Silvera D, Formenti S C, Schneider R J. Translational control in cancer. Nature reviews Cancer. 2010; 10(4): 254-66. Epub 2010/03/25.
19. Baylot V, Andrieu C, Katsogiannou M, Taieb D, Garcia S, Giusiano S, et al. OGX-427 inhibits tumor progression and enhances gemcitabine chemotherapy in pancreatic cancer. Cell death & disease. 2011; 2:e221. Epub 2011/10/21.
20. Furic L, Rong L, Larsson O, Koumakpayi I H, Yoshida K, Brueschke A, et al. eIF4E phosphorylation promotes tumorigenesis and is associated with prostate cancer progression. Proceedings of the National Academy of Sciences of the United States of America. 2010; 107(32): 14134-9. Epub 2010/08/04.
21. Ueda T, Sasaki M, Elia A J, Chio, II, Hamada K, Fukunaga R, et al. Combined deficiency for MAP kinase-interacting kinase 1 and 2 (Mnk1 and Mnk2) delays tumor development. Proceedings of the National Academy of Sciences of the United States of America. 2010; 107(32): 13984-90. Epub 2010/08/04.
22. Ueda T, Watanabe-Fukunaga R, Fukuyama H, Nagata S, Fukunaga R. Mnk2 and Mnk1 are essential for constitutive and inducible phosphorylation of eukaryotic initiation factor 4E but not for cell growth or development. Molecular and cellular biology. 2004; 24(15):6539-49. Epub 2004/07/16.
23. Greenway B A. Effect of flutamide on survival in patients with pancreatic cancer: results of a prospective, randomised, double blind, placebo controlled trial. BMJ. 1998; 316(7149):1935-8. Epub 1998/06/26.
24. Konduri S, Schwarz M A, Cafasso D, Schwarz R E. Androgen receptor blockade in experimental combination therapy of pancreatic cancer. The Journal of surgical research. 2007; 142(2):378-86. Epub 2007/06/15.
25. Negi S S, Agarwal A, Chaudhary A. Flutamide in unresectable pancreatic adenocarcinoma: a randomized, double-blind, placebo-controlled trial. Investigational new drugs. 2006; 24(3):189-94. Epub 2005/09/01.
26. Targarona E M, Pons M D, Gonzalez G, Boix L, Marco V, Marco C. Is exocrine pancreatic cancer a hormone-dependent tumor? A study of the existence of sex hormone receptors in normal and neoplastic pancreas. Hepato-gastroenterology. 1991; 38(2):165-9. Epub 1991/04/01.
27. Fogar P, Basso D, Pasquali C, Piva M G, Brigato L, De Paoli M, et al. Portal but not peripheral serum levels of interleukin 6 could interfere with glucose metabolism in patients with pancreatic cancer. Clinica chimica acta; international journal of clinical chemistry. 1998; 277(2): 181-9. Epub 1998/12/16.
28. Nacusi L P, Debes J D. Primers on molecular pathways: nuclear receptors in pancreatic cancer. The ligand-independent way. Pancreatology. 2008; 8(4-5):422-4. Epub 2008/08/21.
29. Moore M J, Goldstein D, Hamm J, Figer A, Hecht J R, Gallinger S, et al. Erlotinib plus gemcitabine compared with gemcitabine alone in patients with advanced pancreatic cancer: a phase III trial of the National Cancer Institute of Canada Clinical Trials Group. Journal of clinical oncology: official journal of the American Society of Clinical Oncology. 2007; 25(15):1960-6. Epub 2007/04/25.
30. Bao B, Ali S, Kong D, Sarkar S H, Wang Z, Banerjee S, et al. Anti-tumor activity of a novel compound-CDF is mediated by regulating miR-21, miR-200, and PTEN in pancreatic cancer. PloS one. 2011; 6(3):e17850. Epub 2011/03/17.
31. Wang Z, Banerjee S, Ahmad A, Li Y, Azmi A S, Gunn J R, et al. Activated K-ras and INK4a/Arf deficiency cooperate during the development of pancreatic cancer by activation of Notch and NF-kappaB signaling pathways. PloS one. 2011; 6(6):e20537. Epub 2011/06/16.
32. Khan K M, Zia U, Perveen S, Hayat S, Ali M, Voelter W. A convenient iodination method for alcohols using cesium iodide/methanesulfonic acid and its comparison using cesium iodide/p-toluenesulfonic acid or cesium iodide/aluminium chloride. Natural product research. 2008; 22(14):1264-69. Epub 2008/10/22.
33. Bouzide A S G. Highly selective silver(I) oxide mediated monoprotection of symmetrical diols. Tetrahedron Letters. 1997; 38(34):5945-8.
34. Poon K W, Dudley G B. Mix-and-heat benzylation of alcohols using a bench-stable pyridinium salt. The Journal of organic chemistry. 2006; 71(10):3923-7. Epub 2006/05/06.
35. Giannis A, Heretsch P, Sarli V, Stossel A. Synthesis of cyclopamine using a biomimetic and diastereoselective approach. Angewandte Chemie. 2009; 48(42):7911-4. Epub 2009/07/11.
36. Hammerer F, Garcia G, Chen S, Poyer F, Achelle S, Fiorini-Debuisschert C, et al. Synthesis and characterization of glycoconjugated porphyrin triphenylamine hybrids for targeted two-photon photodynamic therapy. The Journal of organic chemistry. 2014; 79(3):1406-17. Epub 2014/01/18.
37. Sun Q, Cai S, Peterson, B R. Practical synthesis of 3beta-amino-5-cholestene and related 3beta-halides involving i-steroid and retro-i-steroid rearrangements. Organic Lettere. 2009; 11:567-70.
38. Ge Y H Y, inventor; Methods and compounds for preparing 3alpha-oxygen substituted steroids 2012.
39. Eric B A L, Patricia R, Jean-Francois C, Jean-Francois G. Convinient and simplified approaches to N-monoprotected triaminopropane derivatives: key intermediate for biofunctional chelating agent synthesis. Synthesis. 1998; 8:111β-8.
40. Zampella A DOR, Sepe V, DeMarino S, Borbone N, Valenti A, Debitus C, Zollo F, D'Auria M V. Isolation of plakinamine 1: A new steroidal alkaloid from marine sponge Corticum sp. and synthesis an analogue model compound. European Journal of Organic Chemistry. 2005; 2005:4359-63.
41. Pastor I M T R, Yus M. Isoprene-mediated lithiation of 1-alkylimidazoles: Chiral induction of the alkyl substituent. Letters in Organic Chemistry. 2010; 7:37β-6.
42. Kotovshchikov Y N L G, Lukashev N V, Beletskaya I P. An efficient approach to azolyl-substituted steroids through copper-catalyzed Ullmann C—N coupling. European Journal of Organic Chemistry. 2013; 2013:782β-32.
43. Holland H L K S, Tan L, Njar V C O. Synthesis of 6-hydroxyamino-3-oxo steroids, a new class of aromatase inhibitors. Journal of Chemical Society, Perkin Trans 1. 1992:585-7.
44. Njar V C O H R, Robinson C H. Synthesis of 6alpha,7alpha and 6beta,7beta-aziridinoandrost-4-ene-3,17-diones and related compounds: potential aromatase inhibitors. Journal of Chemical Society, Perkin Trans 1. 1995: 985-91.
45. Chou T C. Drug combination studies and their synergy quantification using the Chou-Talalay method. Cancer research. 2010; 70(2):440-6. Epub 2010/01/14.
46. Godbole A M, Purushottamachar P, Martin M S, Daskalakis C, Njar V C. Autophagy inhibition synergistically enhances anticancer efficacy of RAMBA, VN/12-1 in SKBR-3 cells, and tumor xenografts. Molecular cancer therapeutics. 2012; 11(4):898-908. Epub 2012/02/16.
47. Godbole A M, Ramalingam S, Ramamurthy V P, Khandelwal A, Bruno R D, Upreti V V, et al. VN/14-1 induces ER stress and autophagy in HP-LTLC human breast cancer cells and has excellent oral pharmacokinetic profile in female Sprague Dawley rats. European journal of pharmacology. 2014; 734:98-104. Epub 2014/04/15.
48. Khandelwal A, Gediya L, Njar V. MS-275 synergistically enhances the growth inhibitory effects of RAMBA VN/66-1 in hormone-insensitive PC-3 prostate cancer cells and tumours. British journal of cancer. 2008; 98(7): 1234-43. Epub 2008/03/20.
49. Miyabayashi K, Ijichi H, Mohri D, Tada M, Yamamoto K, Asaoka Y, et al. Erlotinib prolongs survival in pancreatic cancer by blocking gemcitabine-induced MAPK signals. Cancer research. 2013; 73(7):2221-34. Epub 2013/02/05.
50. Yang S, Wang X, Contino G, Liesa M, Sahin E, Ying H, et al. Pancreatic cancers require autophagy for tumor growth. Genes & development. 2011; 25(7):717-29. Epub 2011/03/17.
51. Guo J Y, Chen H Y, Mathew R, Fan J, Strohecker A M, Karsli-Uzunbas G, et al. Activated Ras requires autophagy to maintain oxidative metabolism and tumorigenesis. Genes & development. 2011; 25(5):460-70. Epub 2011/02/15.
52. Lock R, Roy S, Kenific C M, Su J S, Salas E, Ronen S M, et al. Autophagy facilitates glycolysis during Rasmediated oncogenic transformation. Molecular biology of the cell. 2011; 22(2):165-78. Epub 2010/12/02.
53. Boutin B, Taj eddine N, Vandersmissen P, Zanou N, Van Schoor M, Mondin L, et al. Androgen deprivation and androgen receptor competition by bicalutamide induce autophagy of hormone-resistant prostate cancer cells and confer resistance to apoptosis. The Prostate. 2013; 73(10): 1090-102. Epub 2013/03/28.
54. Konicek B W, Stephens J R, McNulty A M, Robichaud N, Peery R B, Dumstorf C A, et al. Therapeutic inhibition of MAP kinase interacting kinase blocks eukaryotic initiation factor 4E phosphorylation and suppresses outgrowth of experimental lung metastases. Cancer research. 2011; 71(5):1849-57. Epub 2011/01/15.
55. Dan H C, Cooper M J, Cogswell P C, Duncan J A, Ting J P, Baldwin A S. Akt-dependent regulation ofNF-{kappa}B is controlled by mTOR and Raptor in association with IKK. Genes & development. 2008; 22(11): 1490-500. Epub 2008/06/04.
56. El-Rayes B F, Ali S, Ali I F, Philip P A, Abbruzzese J, Sarkar F H. Potentiation of the effect of erlotinib by genistein in pancreatic cancer: the role of Akt and nuclear factor-kappaB. Cancer research. 2006; 66(21): 10553-9. Epub 2006/11/03.
57. Zhou J, Wang C Y, Liu T, Wu B, Zhou F, Xiong J X, et al. Persistence of side population cells with high drug efflux capacity in pancreatic cancer. World journal of gastroenterology: WJG. 2008; 14(6):925-30. Epub 2008/02/02.
58. El Maalouf G, Le Tourneau C, Batty G N, Faivre S, Raymond E. Markers involved in resistance to cytotoxics and targeted therapeutics in pancreatic cancer. Cancer treatment reviews. 2009; 35(2):167-74. Epub 2008/11/26.
59. Ali S, Ahmad A, Banerjee S, Padhye S, Dominiak K, Schaffert J M, et al. Gemcitabine sensitivity can be induced in pancreatic cancer cells through modulation of miR-200 and miR-21 expression by curcumin or its analogue CDF. Cancer research. 2010; 70(9):3606-17. Epub 2010/04/15.

60. Singh A, Greninger P, Rhodes D, Koopman L, Violette S, Bardeesy N, et al. A gene expression signature associated with "K-Ras addiction" reveals regulators of EMT and tumor cell survival. Cancer cell. 2009; 15(6):489-500. Epub 2009/05/30.
61. Collins M A, Bednar F, Zhang Y, Brisset J C, Galban S, Galban C J, et al. Oncogenic Kras is required for both the initiation and maintenance of pancreatic cancer in mice. The Journal of clinical investigation. 2012; 122(2):639-53. Epub 2012/01/11.
62. Bruno R D, Vasaitis T S, Gediya L K, Purushottamachar P, Godbole A M, Ates-Alagoz Z, et al. Synthesis and biological evaluations of putative metabolically stable analogs of VN/124-1 (TOK-001): head to head anti-tumor efficacy evaluation of VN/124-1 (TOK-001) and abiraterone in LAPC-4 human prostate cancer xenograft model. Steroids. 2011; 76(12):1268-79. Epub 2011/07/07.
63. Handratta V D, Vasaitis T S, Njar V C, Gediya L K, Kataria R, Chopra P, et al. Novel C-17-heteroaryl steroidal CYP17 inhibitors/antiandrogens: synthesis, in vitro biological activity, pharmacokinetics, and antitumor activity in the LAPC4 human prostate cancer xenograft model. Journal of medicinal chemistry. 2005; 48(8):2972-84. Epub 2005/04/15.
64. Schayowitz A, Sabnis G, Goloubeva O, Njar V C, Brodie A M. Prolonging hormone sensitivity in prostate cancer xenografts through dual inhibition of AR and mTOR. British journal of cancer. 2010; 103(7):1001-7. Epub 2010/09/16.
65. Vasaitis T, Belosay A, Schayowitz A, Khandelwal A, Chopra P, Gediya L K, et al. Androgen receptor inactivation contributes to antitumor efficacy of 17 {alpha}-hydroxylase/17,20-lyase inhibitor 3beta-hydroxy-17-(1H-benzimidazole-1-yl)androsta-5,16-diene in prostate cancer. Molecular cancer therapeutics. 2008; 7(8):2348-57. Epub 2008/08/30.
66. Azmi A S, Aboukameel A, Bao B, Sarkar F H, Philip P A, Kauffman M, et al. Selective inhibitors of nuclear export block pancreatic cancer cell proliferation and reduce tumor growth in mice. Gastroenterology. 2013; 144(2):447-56. Epub 2012/10/24.
67. Bao B, Wang Z, Ali S, Ahmad A, Azmi A S, Sarkar S H, et al. Metformin inhibits cell proliferation, migration and invasion by attenuating CSC function mediated by deregulating miRNAs in pancreatic cancer cells. Cancer prevention research. 2012; 5(3):355-64. Epub 2011/11/17.
68. Muders M H, Vohra P K, Dutta S K, Wang E, Ikeda Y, Wang L, et al. Targeting GIPC/synectin in pancreatic cancer inhibits tumor growth. Clinical cancer research: an official journal of the American Association for Cancer Research. 2009; 15(12):4095-103. Epub 2009/06/11.
69. Wang W, Qin J J, Voruganti S, Wang M H, Sharma H, Patil S, et al. Identification of a New Class of MDM2 Inhibitor That Inhibits Growth of Orthotopic Pancreatic Tumors in Mice. Gastroenterology. 2014. Epub 2014/07/13.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A pharmaceutical composition for treating pancreatic cancer, comprising:
a compound that is at least one selected from the group consisting of

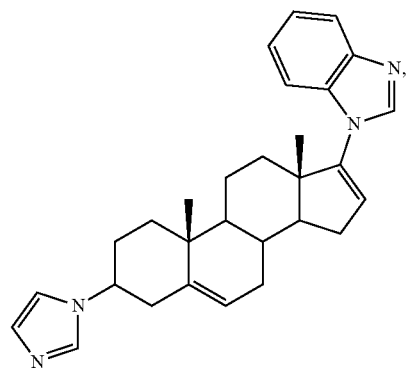

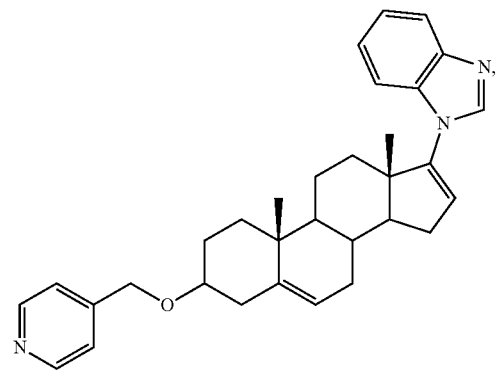

and a pharmaceutically acceptable salt thereof.

2. The pharmaceutical composition according to claim 1, wherein the pharmaceutical composition further comprises

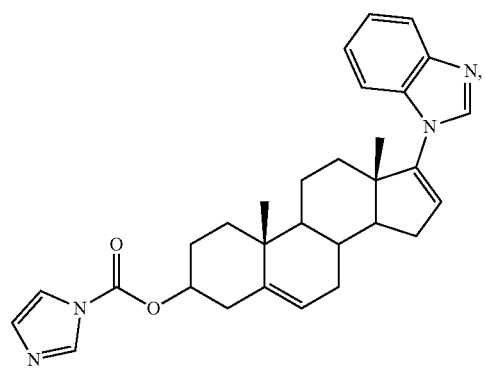 [SMILES: C[C@]12CCC(OC(=O)n3ccnc3)CC1=CCC1C2CC[C@]2(C)C(n3cnc4ccccc43)=CCC12]

or a pharmaceutically acceptable salt thereof.

3. The pharmaceutical composition according to claim 1, wherein the pharmaceutical composition comprises

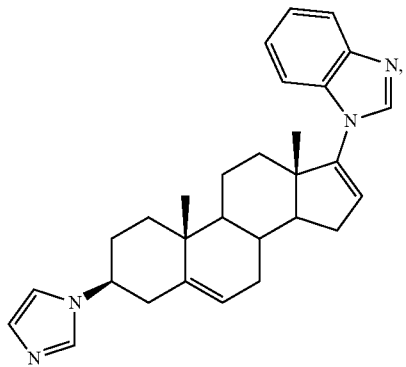 [SMILES: C[C@]12CC[C@H](n3ccnc3)CC1=CCC1C2CC[C@]2(C)C(n3cnc4ccccc43)=CCC12]

or the pharmaceutically acceptable salt thereof.

4. The pharmaceutical composition according to claim 1, wherein the pharmaceutical composition comprises

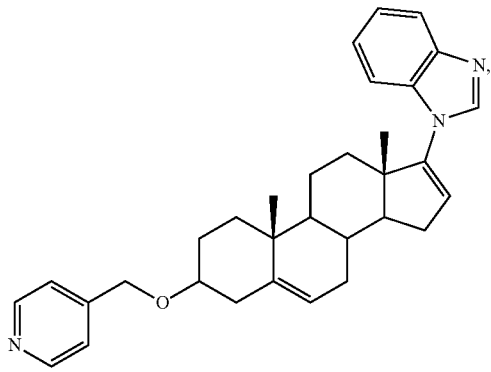 [SMILES: C[C@]12CCC(OCc3ccncc3)CC1=CCC1C2CC[C@]2(C)C(n3cnc4ccccc43)=CCC12]

or the pharmaceutically acceptable salt thereof.

5. The pharmaceutical composition according to claim 1, wherein the pharmaceutical acceptable salt is a hydrochloride salt or an acetic acid salt.

6. The pharmaceutical composition according to claim 1, wherein the pharmaceutical composition further comprises polyvinylpyrrolidone, and wherein a ratio of the compound or the pharmaceutically acceptable salt thereof to the polyvinylpyrrolidone is from 1:2 to 2:1.

7. The pharmaceutical composition according to claim 1, wherein the pancreatic cancer is pancreatic adenocarcinoma.

8. The pharmaceutical composition according to claim 7, wherein the pancreatic adenocarcinoma is pancreatic ductal adenocarcinoma (PDAC) or pancreatic invasive adenocarcinoma.

9. The pharmaceutical composition according to claim 7, wherein the pancreatic adenocarcinoma is gemcitabine resistant.

10. The pharmaceutical composition according to claim 7, wherein the pancreatic adenocarcinoma is gemcitabine naive.

11. The pharmaceutical composition according to claim 7, wherein the pancreatic adenocarcinoma is gemcitabine/erlotinib resistant.

12. The pharmaceutical composition according to claim 1, wherein the pancreatic cancer is androgen dependent.

13. The pharmaceutical composition according to claim 1, further comprising a chemotherapeutic agent.

14. The pharmaceutical composition according to claim 12, wherein the chemotherapeutic agent is gemcitabine.

* * * * *